US011433131B2

(12) United States Patent
Mirkin et al.

(10) Patent No.: US 11,433,131 B2
(45) Date of Patent: Sep. 6, 2022

(54) ADOPTIVE CELL THERAPY USING SPHERICAL NUCLEIC ACIDS (SNAS)

(71) Applicant: Northwestern University, Evanston, IL (US)

(72) Inventors: Chad A. Mirkin, Wilmette, IL (US); Andrew Lee, Chicago, IL (US); Bin Zhang, Chicago, IL (US); Donye Dominguez, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 16/611,502

(22) PCT Filed: May 11, 2018

(86) PCT No.: PCT/US2018/032372
§ 371 (c)(1),
(2) Date: Nov. 7, 2019

(87) PCT Pub. No.: WO2018/209270
PCT Pub. Date: Nov. 15, 2018

(65) Prior Publication Data
US 2020/0101156 A1    Apr. 2, 2020

Related U.S. Application Data

(60) Provisional application No. 62/505,092, filed on May 11, 2017.

(51) Int. Cl.
*C07H 21/04* (2006.01)
*A61K 39/39* (2006.01)
*A61P 35/00* (2006.01)
*A61K 39/00* (2006.01)
*C12N 15/113* (2010.01)

(52) U.S. Cl.
CPC ...... *A61K 39/39* (2013.01); *A61K 39/001192* (2018.08); *A61P 35/00* (2018.01); *C12N 15/1138* (2013.01); *A61K 2039/55555* (2013.01); *A61K 2039/55561* (2013.01); *C12N 2310/11* (2013.01); *C12N 2310/141* (2013.01); *C12N 2310/532* (2013.01)

(58) Field of Classification Search
USPC ......................................................... 514/44
See application file for complete search history.

(56) References Cited

U.S. PATENT DOCUMENTS

| | | |
|---|---|---|
| 3,687,808 A | 8/1972 | Merigan et al. |
| 4,179,337 A | 12/1979 | Davis et al. |
| 4,289,872 A | 9/1981 | Denkewalter et al. |
| 4,489,055 A | 12/1984 | Couvreur et al. |
| 4,845,205 A | 7/1989 | Huynh Dinh et al. |
| 4,904,582 A | 2/1990 | Tullis |
| 4,958,013 A | 9/1990 | Letsinger |
| 5,112,963 A | 5/1992 | Pieles et al. |
| 5,130,302 A | 7/1992 | Spielvogel et al. |
| 5,134,066 A | 7/1992 | Rogers et al. |
| 5,138,045 A | 8/1992 | Cook et al. |
| 5,175,273 A | 12/1992 | Bischofberger et al. |
| 5,218,105 A | 6/1993 | Cook et al. |
| 5,229,490 A | 7/1993 | Tam |
| 5,245,022 A | 9/1993 | Weis et al. |
| 5,256,775 A | 10/1993 | Froehler |
| 5,258,506 A | 11/1993 | Urdea et al. |
| 5,367,066 A | 11/1994 | Urdea et al. |
| 5,432,272 A | 7/1995 | Benner |
| 5,457,187 A | 10/1995 | Gmeiner et al. |
| 5,459,255 A | 10/1995 | Cook et al. |
| 5,472,881 A | 12/1995 | Beebe et al. |
| 5,484,908 A | 1/1996 | Froehler et al. |
| 5,491,133 A | 2/1996 | Walder et al. |
| 5,502,177 A | 3/1996 | Matteucci et al. |
| 5,525,711 A | 6/1996 | Hawkins et al. |
| 5,545,730 A | 8/1996 | Urdea et al. |
| 5,552,540 A | 9/1996 | Haralambidis |
| 5,574,142 A | 11/1996 | Meyer, Jr. et al. |
| 5,576,427 A | 11/1996 | Cook et al. |
| 5,578,718 A | 11/1996 | Cook et al. |
| 5,587,361 A | 12/1996 | Cook et al. |
| 5,587,371 A | 12/1996 | Sessler et al. |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,623,065 A | 4/1997 | Cook et al. |
| 5,645,985 A | 7/1997 | Froehler et al. |
| 5,652,356 A | 7/1997 | Agrawal |
| 5,681,941 A | 10/1997 | Cook et al. |
| 5,688,941 A | 11/1997 | Cook et al. |
| 5,700,922 A | 12/1997 | Cook |
| 5,750,692 A | 5/1998 | Cook et al. |
| 5,763,588 A | 6/1998 | Matteucci et al. |
| 5,830,653 A | 11/1998 | Froehler et al. |
| 6,005,096 A | 12/1999 | Matteucci et al. |
| 6,080,580 A | 6/2000 | Baker et al. |
| 6,228,642 B1 | 5/2001 | Baker et al. |
| 6,287,860 B1 | 9/2001 | Monia et al. |

(Continued)

FOREIGN PATENT DOCUMENTS

EP    1072679 A2    1/2001
EP    1628531 A2    3/2006

(Continued)

OTHER PUBLICATIONS

Kapadia, Chintan H., Jilian R. Melamed, and Emily S. Day. "Spherical nucleic acid nanoparticles: Therapeutic potential." BioDrugs 32.4 (2018): 297-309.*

(Continued)

Primary Examiner — Kimberly Chong
(74) Attorney, Agent, or Firm — Marshall, Gerstein & Borun LLP

(57) ABSTRACT

The disclosure is related to compositions comprising a cell and a spherical nucleic acid (SNA) comprising a nanoparticle, an oligonucleotide on the surface of the nanoparticle, and an antigen; and to methods for production of such compositions and their applications, including but not limited to adoptive cell therapy.

32 Claims, 8 Drawing Sheets

Specification includes a Sequence Listing.

(56) References Cited

U.S. PATENT DOCUMENTS

| | | |
|---|---|---|
| 6,417,340 B1 | 7/2002 | Mirkin et al. |
| 6,495,324 B1 | 12/2002 | Mirkin et al. |
| 6,582,921 B2 | 6/2003 | Mirkin et al. |
| 6,602,669 B2 | 8/2003 | Letsinger et al. |
| 6,610,491 B2 | 8/2003 | Mirkin et al. |
| 6,849,725 B2 | 2/2005 | Junghans et al. |
| 7,001,616 B2 | 2/2006 | Batich et al. |
| 7,176,296 B2 | 2/2007 | Agrawal et al. |
| 7,223,833 B1 | 5/2007 | Nielsen et al. |
| 7,238,472 B2 | 7/2007 | Mirkin et al. |
| 7,262,286 B2 | 8/2007 | Kandimalla et al. |
| 7,276,489 B2 | 10/2007 | Agrawal et al. |
| 7,291,284 B2 | 11/2007 | Mirkin et al. |
| 7,332,586 B2 | 2/2008 | Franzen et al. |
| 7,354,907 B2 | 4/2008 | Agrawal et al. |
| 7,404,969 B2 | 7/2008 | Chen et al. |
| 7,470,674 B2 | 12/2008 | Agrawal et al. |
| 7,514,099 B2 | 4/2009 | Chen et al. |
| 7,569,554 B2 | 8/2009 | Kandimalla et al. |
| 7,709,617 B2 | 5/2010 | Kandimalla et al. |
| 7,713,535 B2 | 5/2010 | Agrawal et al. |
| 7,745,606 B2 | 6/2010 | Dina et al. |
| 7,776,834 B2 | 8/2010 | Agrawal et al. |
| 7,786,089 B2 | 8/2010 | Kandimalla et al. |
| 7,833,992 B2 | 11/2010 | Vargeese et al. |
| 7,851,453 B2 | 12/2010 | Agrawal et al. |
| 7,875,594 B2 | 1/2011 | Kandimalla et al. |
| 7,884,197 B2 | 2/2011 | Kandimalla et al. |
| 7,956,176 B2 | 6/2011 | McSwiggen et al. |
| 7,960,362 B2 | 6/2011 | Kandimalla et al. |
| 7,964,578 B2 | 6/2011 | Vargeese et al. |
| 7,993,659 B2 | 8/2011 | Noelle et al. |
| 8,008,266 B2 | 8/2011 | Krieg et al. |
| 8,008,267 B2 | 8/2011 | Kandimalla et al. |
| 8,008,449 B2 | 8/2011 | Korman et al. |
| 8,017,591 B2 | 9/2011 | Brzezicha et al. |
| 8,114,419 B2 | 2/2012 | Krieg |
| 8,128,944 B2 | 3/2012 | Jurk et al. |
| 8,188,261 B2 | 5/2012 | Kandimalla et al. |
| 8,202,850 B2 | 6/2012 | Agrawal et al. |
| 8,202,979 B2 | 6/2012 | McSwiggen et al. |
| 8,273,866 B2 | 9/2012 | McSwiggen et al. |
| 8,283,328 B2 | 10/2012 | Krieg et al. |
| 8,304,396 B2 | 11/2012 | Krieg et al. |
| 8,362,233 B2 | 1/2013 | Kandimalla et al. |
| 8,420,615 B2 | 4/2013 | Agrawal et al. |
| 8,431,544 B1 | 4/2013 | Agrawal et al. |
| 8,466,124 B2 | 6/2013 | Jurk et al. |
| 8,476,416 B2 | 7/2013 | Kandimalla et al. |
| 8,853,375 B2 | 10/2014 | Kandimalla et al. |
| 8,871,436 B2 | 10/2014 | Lopez |
| 8,946,175 B1 | 2/2015 | Kandimalla et al. |
| 8,987,221 B2 | 3/2015 | Zhu et al. |
| 9,139,827 B2 | 9/2015 | Mirkin et al. |
| 9,169,325 B2 | 10/2015 | Keler et al. |
| 9,192,667 B2 | 11/2015 | Hoves et al. |
| 9,200,287 B2 | 12/2015 | Uhlmann et al. |
| 9,212,366 B2 | 12/2015 | Wittig et al. |
| 9,265,729 B2 | 2/2016 | Nakamura |
| 9,364,443 B2 | 6/2016 | Beduneau et al. |
| 9,421,254 B2 | 8/2016 | Berzofsky et al. |
| 9,422,564 B2 | 8/2016 | Dina et al. |
| 9,499,815 B1 | 11/2016 | Schroff et al. |
| 9,506,056 B2 | 11/2016 | Mirkin et al. |
| 9,522,958 B2 | 12/2016 | Epstein et al. |
| 9,532,948 B2 | 1/2017 | Mirkin et al. |
| 9,549,901 B2 | 1/2017 | Shi et al. |
| 9,580,708 B2 | 2/2017 | Uhlmann et al. |
| 9,617,541 B2 | 4/2017 | Mirkin et al. |
| 9,844,562 B2 | 12/2017 | Mirkin et al. |
| 9,889,209 B2 | 2/2018 | Mirkin et al. |
| 9,950,064 B2 | 4/2018 | Ott et al. |
| 9,993,495 B2 | 6/2018 | Guiducci et al. |
| 10,098,958 B2 | 10/2018 | Mirkin et al. |
| 10,117,919 B2 | 11/2018 | Knutson et al. |
| 10,149,905 B2 | 12/2018 | Gemba et al. |
| 10,155,950 B2 | 12/2018 | Munnes et al. |
| 10,182,988 B2 | 1/2019 | Mirkin et al. |
| 10,246,715 B1 | 4/2019 | Chuang et al. |
| 10,280,424 B2 | 5/2019 | Kleuss et al. |
| 10,323,091 B2 | 6/2019 | van Dijk et al. |
| 10,369,220 B2 | 8/2019 | Kaplan |
| 10,370,656 B2 | 8/2019 | Mirkin et al. |
| 10,391,116 B2 | 8/2019 | Mirkin et al. |
| 10,398,784 B2 | 9/2019 | Mirkin et al. |
| 10,435,469 B2 | 10/2019 | Goldberg et al. |
| 10,449,212 B2 | 10/2019 | Hanagata et al. |
| 10,456,463 B2 | 10/2019 | Davis et al. |
| 10,463,686 B2 | 11/2019 | Agrawal et al. |
| 10,487,333 B2 | 11/2019 | Schroff et al. |
| 10,617,749 B1 | 4/2020 | Hanks et al. |
| 10,632,193 B2 | 4/2020 | McCreedy |
| 10,646,576 B2 | 5/2020 | Pascolo |
| 10,653,780 B2 | 5/2020 | Hope et al. |
| 10,660,954 B2 | 5/2020 | Mitchell et al. |
| 10,669,338 B2 | 6/2020 | Chang et al. |
| 10,682,365 B2 | 6/2020 | Krieg |
| 10,695,400 B2 | 6/2020 | Jamal |
| 10,722,537 B2 | 7/2020 | Masopust, Jr. et al. |
| 10,736,848 B2 | 8/2020 | Von Andrian et al. |
| 10,738,100 B2 | 8/2020 | Schuster et al. |
| 10,738,120 B2 | 8/2020 | Wilm et al. |
| 10,751,291 B2 | 8/2020 | Fahmy et al. |
| 10,751,412 B2 | 8/2020 | Yu et al. |
| 10,751,424 B2 | 8/2020 | Baumhof et al. |
| 10,758,482 B2 | 9/2020 | Hakim et al. |
| 10,758,624 B2 | 9/2020 | Kortylewski et al. |
| 10,765,690 B2 | 9/2020 | Cluff et al. |
| 10,772,907 B2 | 9/2020 | Agrawal et al. |
| 10,792,251 B2 | 10/2020 | Mirkin et al. |
| 10,822,415 B2 | 11/2020 | Levade et al. |
| 10,828,353 B2 | 11/2020 | Zhao et al. |
| 10,835,550 B2 | 11/2020 | Agrawal et al. |
| 10,836,826 B2 | 11/2020 | Goldberg et al. |
| 10,849,963 B2 | 12/2020 | Kroczek |
| 10,851,379 B2 | 12/2020 | Munnes et al. |
| 10,869,885 B2 | 12/2020 | Wagner |
| 10,881,612 B2 | 1/2021 | Serda et al. |
| 2003/0022848 A1 | 1/2003 | Baker et al. |
| 2003/0147966 A1 | 8/2003 | Franzen et al. |
| 2003/0212026 A1 | 11/2003 | Krieg et al. |
| 2004/0131628 A1 | 7/2004 | Bratzler et al. |
| 2004/0247680 A1 | 12/2004 | Farokhzad et al. |
| 2005/0089890 A1 | 4/2005 | Cubicciotti |
| 2005/0096263 A1 | 5/2005 | Keay et al. |
| 2005/0130911 A1 | 6/2005 | Uhlmann et al. |
| 2005/0136258 A1 | 6/2005 | Nie et al. |
| 2005/0197315 A1 | 9/2005 | Taira et al. |
| 2005/0244858 A1 | 11/2005 | Rossi et al. |
| 2006/0002949 A1 | 1/2006 | Glenn et al. |
| 2006/0008907 A1 | 1/2006 | Friedman et al. |
| 2006/0019917 A1 | 1/2006 | Guerciolini et al. |
| 2006/0035344 A1 | 2/2006 | Pachuk et al. |
| 2006/0105343 A1 | 5/2006 | Zetter et al. |
| 2006/0142556 A1 | 6/2006 | Agrawal |
| 2006/0159921 A1 | 7/2006 | Murthy et al. |
| 2006/0183247 A1 | 8/2006 | Kim et al. |
| 2006/0188560 A1 | 8/2006 | Cheresh et al. |
| 2006/0233712 A1 | 10/2006 | Penades et al. |
| 2006/0252037 A1 | 11/2006 | Kolesnick et al. |
| 2006/0275371 A1 | 12/2006 | Dai et al. |
| 2007/0049546 A1 | 3/2007 | Brzezicha et al. |
| 2007/0093439 A1 | 4/2007 | Agrawal et al. |
| 2007/0243132 A1 | 10/2007 | Russell-Jones et al. |
| 2008/0045473 A1 | 2/2008 | Uhlmann et al. |
| 2008/0057128 A1 | 3/2008 | Li et al. |
| 2008/0097092 A1 | 4/2008 | Khvorova et al. |
| 2008/0213177 A1 | 9/2008 | Rademacher et al. |
| 2008/0279785 A1 | 11/2008 | Kandimalla et al. |
| 2008/0305106 A1 | 12/2008 | Brennan et al. |
| 2008/0317768 A1 | 12/2008 | Bianchi |
| 2009/0035576 A1 | 2/2009 | Prasad et al. |
| 2009/0081244 A1 | 3/2009 | Glenn et al. |
| 2009/0148384 A1 | 6/2009 | Fischer et al. |

(56) References Cited

U.S. PATENT DOCUMENTS

| | | |
|---|---|---|
| 2009/0155173 A1 | 6/2009 | Scherman et al. |
| 2009/0209629 A1 | 8/2009 | Mirkin et al. |
| 2009/0286853 A1 | 11/2009 | Gryaznov et al. |
| 2009/0299045 A1 | 12/2009 | Richards et al. |
| 2010/0111968 A1 | 5/2010 | Branigan et al. |
| 2010/0167051 A1 | 7/2010 | Goia et al. |
| 2010/0183504 A1 | 7/2010 | Chen |
| 2010/0183634 A1 | 7/2010 | Luo et al. |
| 2010/0203142 A1 | 8/2010 | Zhang et al. |
| 2010/0267814 A1 | 10/2010 | Bennett et al. |
| 2010/0303803 A1 | 12/2010 | Schroff et al. |
| 2011/0009477 A1 | 1/2011 | Yu et al. |
| 2011/0034422 A1 | 2/2011 | Kannan et al. |
| 2011/0158937 A1 | 6/2011 | Kandimalla et al. |
| 2011/0201594 A1 | 8/2011 | Murthi et al. |
| 2011/0223257 A1 | 9/2011 | Zhao et al. |
| 2011/0244026 A1 | 10/2011 | Guild et al. |
| 2011/0262347 A1 | 10/2011 | Ruoslahti et al. |
| 2011/0305684 A1 | 12/2011 | Agrawal et al. |
| 2012/0093804 A1 | 4/2012 | Schroff et al. |
| 2012/0107303 A1 | 5/2012 | Kandimalla et al. |
| 2012/0201807 A1 | 8/2012 | Agrawal et al. |
| 2012/0258140 A1 | 10/2012 | Jurk et al. |
| 2012/0282186 A1 | 11/2012 | Mirkin et al. |
| 2013/0095039 A1 | 4/2013 | Lu et al. |
| 2013/0136714 A1 | 5/2013 | Wang et al. |
| 2013/0178610 A1 | 7/2013 | Mirkin et al. |
| 2013/0178611 A1 | 7/2013 | Seya et al. |
| 2013/0287814 A1 | 10/2013 | Schroff et al. |
| 2016/0123964 A1 | 5/2016 | Tumeh et al. |
| 2016/0310425 A1 | 10/2016 | Mirkin et al. |
| 2017/0044544 A1 | 2/2017 | Mirkin et al. |
| 2017/0130231 A1 | 5/2017 | Chae et al. |
| 2017/0182139 A1 | 6/2017 | McNeel et al. |
| 2017/0232109 A1 | 8/2017 | Mirkin et al. |
| 2017/0326232 A1 | 11/2017 | Guiducci et al. |
| 2017/0333542 A1 | 11/2017 | Erickson |
| 2018/0000851 A1 | 1/2018 | Krieg |
| 2018/0161427 A1 | 6/2018 | Yu et al. |
| 2018/0169229 A1 | 6/2018 | Yu et al. |
| 2018/0200381 A1 | 7/2018 | Kannan et al. |
| 2018/0264105 A1 | 9/2018 | Kugimiya et al. |
| 2018/0280539 A1 | 10/2018 | Debs et al. |
| 2018/0312536 A1 | 11/2018 | Sakamuri et al. |
| 2018/0312837 A1 | 11/2018 | Kortylewski et al. |
| 2018/0340025 A1 | 11/2018 | Dranoff et al. |
| 2018/0344873 A1 | 12/2018 | Mirkin et al. |
| 2018/0371093 A1 | 12/2018 | Bilic et al. |
| 2019/0030150 A1 | 1/2019 | Rekoske |
| 2019/0030185 A1 | 1/2019 | Mirkin et al. |
| 2019/0031756 A1 | 1/2019 | Levade et al. |
| 2019/0046638 A1 | 2/2019 | Krieg |
| 2019/0048342 A1 | 2/2019 | Wang et al. |
| 2019/0077856 A1 | 3/2019 | Scheinberg et al. |
| 2019/0134172 A1 | 5/2019 | Gunn et al. |
| 2019/0160173 A1 | 5/2019 | Gryaznov et al. |
| 2019/0201334 A1 | 7/2019 | Hakim et al. |
| 2019/0209604 A1 | 7/2019 | Zhang et al. |
| 2019/0216816 A1 | 7/2019 | Kutok |
| 2019/0275166 A1 | 9/2019 | Mirkin et al. |
| 2019/0321613 A1 | 10/2019 | Jones et al. |
| 2019/0351053 A1 | 11/2019 | Lamprecht et al. |
| 2020/0031930 A1 | 1/2020 | Goldberg et al. |
| 2020/0079860 A1 | 3/2020 | Khalil et al. |
| 2020/0101156 A1 | 4/2020 | Mirkin et al. |
| 2020/0138945 A1 | 5/2020 | Korman et al. |
| 2020/0222557 A1 | 7/2020 | Berlin et al. |
| 2020/0230234 A1 | 7/2020 | Schroff et al. |
| 2020/0263261 A1 | 8/2020 | Guan et al. |
| 2020/0268786 A1 | 8/2020 | Greenbaum et al. |
| 2020/0281953 A1 | 9/2020 | Krieg |
| 2020/0291394 A1 | 9/2020 | Mirkin et al. |
| 2020/0368349 A1 | 11/2020 | Abdiche et al. |
| 2020/0377879 A1 | 12/2020 | Meyerson et al. |
| 2020/0384104 A1 | 12/2020 | Mirkin et al. |
| 2020/0397695 A1 | 12/2020 | Hakim et al. |
| 2021/0052497 A1 | 2/2021 | Mirkin et al. |

FOREIGN PATENT DOCUMENTS

| | | |
|---|---|---|
| EP | 1674128 A1 | 6/2006 |
| EP | 1350262 B1 | 6/2008 |
| EP | 1408110 B1 | 6/2011 |
| EP | 1807094 B1 | 1/2012 |
| EP | 2451974 A2 | 5/2012 |
| EP | 2405002 B1 | 9/2014 |
| EP | 2759306 B1 | 4/2016 |
| EP | 3313376 A2 | 5/2018 |
| EP | 3209778 B1 | 4/2019 |
| EP | 3492098 A1 | 6/2019 |
| EP | 3566718 A1 | 11/2019 |
| EP | 2244738 B1 | 3/2020 |
| EP | 3411063 B1 | 11/2020 |
| WO | WO 1997/012896 A1 | 4/1997 |
| WO | WO 1998/047343 A2 | 10/1998 |
| WO | WO 2000/043045 A1 | 7/2000 |
| WO | WO 2001/000876 A1 | 1/2001 |
| WO | WO 2001/007055 A2 | 2/2001 |
| WO | WO 2001/049869 A1 | 7/2001 |
| WO | WO 2002/044321 A2 | 6/2002 |
| WO | WO 2002/096262 A2 | 12/2002 |
| WO | WO 03/030941 A1 | 4/2003 |
| WO | WO 2003/051278 A2 | 6/2003 |
| WO | WO 2003/101386 A2 | 12/2003 |
| WO | WO 2004/047870 A1 | 6/2004 |
| WO | WO 2005/008222 A2 | 1/2005 |
| WO | WO 2005/009355 A2 | 2/2005 |
| WO | WO 2005/108616 A1 | 11/2005 |
| WO | WO 2005/116226 A2 | 12/2005 |
| WO | WO 2006/012695 A1 | 2/2006 |
| WO | WO 2006/014653 A1 | 2/2006 |
| WO | WO 2006/015560 A1 | 2/2006 |
| WO | WO 2006/015872 A1 | 2/2006 |
| WO | WO 2006/088833 A2 | 8/2006 |
| WO | WO 2007/047455 A2 | 4/2007 |
| WO | WO 2007/050059 A2 | 5/2007 |
| WO | WO 2007/055682 A2 | 5/2007 |
| WO | WO 2007/055704 A2 | 5/2007 |
| WO | WO 2007/064857 A2 | 6/2007 |
| WO | WO 2007/075626 A2 | 7/2007 |
| WO | WO 2007/084237 A2 | 7/2007 |
| WO | WO 2008/42156 A1 | 4/2008 |
| WO | WO 2008/073959 A2 | 6/2008 |
| WO | WO 2008/097328 A2 | 8/2008 |
| WO | WO 2008/141289 A1 | 11/2008 |
| WO | WO 2008/151049 A2 | 12/2008 |
| WO | WO 2009/018431 A2 | 2/2009 |
| WO | WO 2009/023819 A2 | 2/2009 |
| WO | WO 2009/059805 A1 | 5/2009 |
| WO | WO 2009/105260 A2 | 8/2009 |
| WO | WO 2010/014572 A1 | 2/2010 |
| WO | WO 2010/017152 A2 | 2/2010 |
| WO | WO 2010/017154 A2 | 2/2010 |
| WO | WO 2010/060110 A1 | 5/2010 |
| WO | WO 2010/093705 A2 | 8/2010 |
| WO | WO 2010/125182 A1 | 11/2010 |
| WO | WO 2011/127405 A1 | 10/2011 |
| WO | WO 2011/143608 A1 | 11/2011 |
| WO | WO 2012/085291 A1 | 6/2012 |
| WO | WO 2013/049941 A1 | 4/2013 |
| WO | WO 2013/098813 A1 | 7/2013 |
| WO | WO 2013/177419 A2 | 11/2013 |
| WO | WO 2014/123935 A1 | 8/2014 |
| WO | WO 2014/133547 A1 | 9/2014 |
| WO | WO 2014/191222 A1 | 12/2014 |
| WO | WO 2015/023939 A1 | 2/2015 |
| WO | WO 2015/124614 A1 | 8/2015 |
| WO | WO 2015/126502 A2 | 8/2015 |
| WO | WO 2015/128461 A1 | 9/2015 |
| WO | WO 2015/187966 A1 | 12/2015 |
| WO | WO 2016/081503 A1 | 5/2016 |
| WO | WO 2016/115320 A1 | 7/2016 |
| WO | WO 2016/149323 A1 | 9/2016 |

(56) References Cited

FOREIGN PATENT DOCUMENTS

| WO | WO 2017/42336 A1 | 3/2017 |
|---|---|---|
| WO | WO 2017/050806 A1 | 3/2017 |
| WO | WO 2017/181128 A1 | 10/2017 |
| WO | WO 2018/045058 A1 | 3/2018 |
| WO | WO 2018/064229 A1 | 4/2018 |
| WO | WO 2018/067302 A2 | 4/2018 |
| WO | WO 2018/087699 A2 | 5/2018 |
| WO | WO 2018/152327 A1 | 8/2018 |
| WO | WO 2018/170150 A2 | 9/2018 |
| WO | WO 2018/187791 A1 | 10/2018 |
| WO | WO 2018/189210 A1 | 10/2018 |
| WO | WO 2018/189382 A1 | 10/2018 |
| WO | WO 2018/193137 A1 | 10/2018 |
| WO | WO 2018/203833 A1 | 11/2018 |
| WO | WO 2018/227116 A1 | 12/2018 |
| WO | WO 2019/036031 A2 | 2/2019 |
| WO | WO 2019/038671 A1 | 2/2019 |
| WO | WO 2019/043192 A1 | 3/2019 |
| WO | WO 2019/118883 A1 | 6/2019 |
| WO | WO 2019/126538 A1 | 6/2019 |
| WO | WO 2019/147982 A1 | 8/2019 |
| WO | WO 2019/160866 A2 | 8/2019 |
| WO | WO 2019/169328 A1 | 9/2019 |
| WO | WO 2019/204743 A1 | 10/2019 |
| WO | WO 2019/215151 A1 | 11/2019 |

OTHER PUBLICATIONS

Bielamowicz, Kevin James, Shumaila Khawja, and Nabil Ahmed. "Adoptive cell therapies for glioblastoma." Frontiers in oncology 3 (2013): 275.*
International Search Report and Written Opinion dated Jul. 31, 2018 in connection with PCT/US2018/32372.
International Preliminary Report on Patentability dated Nov. 21, 2019 in connection with PCT/US2018/32372.
[No Author Listed] KeraFAST Chemoselective ligation through copper-free click chemistry. Sep. 21, 2012. published online via http://www.kerafast.com/PDF/Chemoselective_Ligation_Sheet.pdf 2 pages.
Abou-Alfa et al., Randomized phase III study of exatecan and gemcitabine compared with gemcitabine alone in untreated advanced pancreatic cancer, J. Clin. Oneal. 2006; 24(27):4441-7.
Agasti et al., Photoregulated release of caged anticancer drugs from gold nanoparticles, J. Am. Chem. Soc. 2009; 131(16):5728-9.
Agrawal et al., Antisence therapeutics: Is it as simple as complementary base recognition? Mol. Med. Today. 2000; 6: 72-81.
Ahmadi et al., Shape-Controlled Synthesis of Colloidal Platinum Nanoparticles. Science. 1996; 272(5270): 1924-1926.
Aissaoui et al., Efficient topical delivery of plasmid DNA to lung in vivo mediated by putative triggered, PEGylated pDNA nanoparticles, J .Control Release. 154:275-84 (2011).
Altieri, Survivin, versatile modulation of cell division and apoptosis in cancer. Oncogene 2003; 22: 8581-9.
Angelini et al., Reversal of P-glycoprotein-mediated multi drug resistance in human sarcoma MES-SA/Dx-5 cells by nonsteroidal anti-inflammatory drugs. Oneal. Rep. 2008;20(4):731-5.
Anton et al., Design and production of nanoparticles formulated from nano-emulsion templates-a review. J. Control Release. 2008; 128(3):185-99.
Aynie et al., Spongelike alginate nanoparticles as a new potential system for the delivery of antisense oligonucleotides. Antisense Nucl. Acid Drug Dev. 1999; 9: 301-12.
Bahnemann, "Mechanisms of Organic Transformations on Semiconductor Particles," Photochemical Conversion and Storage of Solar Enerqy, 251-276 (1991).
Baker et al., Dendrimer-mediated cell transfection in vitro. Meth. Malec. Biol. 2004;245: 67-81.
Balasubramanian et al., Biodistribution of gold nanoparticles and gene expression changes in the liver and spleen after intravenous administration in rats. Biomaterials. 2010;31(8):2034-42.

Banga et al., Cross-linked micellar spherical nucleic acids from thermoresponsive templates. Journal of the American Chemical Society. Mar. 29, 2017;139(12):4278-81.
Banga et al., Liposomal spherical nucleic acids. J Am Chem Soc. Jul. 16, 2014;136(28):9866-9. doi: 10.1021/ja504845f. Epub Jul. 1, 2014.
Bardeesy et al., Pancreatic cancer biology and genetics, Nat. Rev. Cancer. 2002;2(12):897-909.
Berton et al., Highly loaded nanoparticulate carrier using an hydrophobic antisense oligonucleotide complex. Eur. J. Pharma. Sci. 1999;9:163-70.
Bharali et al., Organically modified silica nanoparticles: a nonviral vector for in vivo gene delivery and expression in the brain. Proc. Natl. Acad. Sci. USA. 2005;102(32): 11539-44.
Bisht et al., Polymeric nanoparticle-encapsulated curcumin ("nanocurcumin"): a novel strategy for human cancer therapy. J. Nanobiotechnology. 2007;5:3. 18 pages.
Bonoiu et al., Nanotechnology approach for drug addiction therapy: gene silencing using delivery of gold nanorod-siRNA nanoplex in dopaminergic neurons. Proc Natl Acad Sci U S A. Apr. 7, 2009;106(14):5546-50. doi:; 10.1073/pnas.0901715106. Epub Mar. 23, 2009.
Brus, Quantum Crystallites and Nonlinear Optics. Appl. Phys. A. 1991;53:465-474.
Burgess, Liposome preparation—Avanti® Polar Lipids. Sigma-Aldrich. 1998. 3 pages.
Calabrese et al., Biocompatible infinite-coordination-polymer nanoparticle-nucleic-acid conjugates for antisense gene regulation. Angew Chem Int Ed Engl. Jan. 7, 2015;54(2):476-480. doi: 10.1002/anie.201407946. Epub Nov. 13, 2014.
Capaccioli et al., Cationic lipids improve antisense oligonucleotide uptake and prevent degradation in cultured cells and inhuman serum. Biochem. Biophys. Res. Commun. 1993;197(2): 818-25.
Carson et al., Hydroxymethyluracil modifications enhance the flexibility and hydrophilicity of double-stranded DNA, Nucleic Acids Res. 44:2085-92 (2016).
Cha et al., Hepatocellular carcinoma: current management. Curr. Probl. Surg. 2010;47(1):10-67.
Chari et al., Immunoconjugates containing novel maytansinoids: promising anticancer drugs. Cancer Res. 1992;52(1):127-31.
Chavany et al., Polyalkylcyanoacrylate nanoparticles as polymeric carriers for antisense oligonucleotides. Pharma. Res. 1992;9(4): 441-9.
Chavany, et al., Adsorption of oligonucleotides onto polyisohexylcyanoacrylate nanoparticles protects them against nucleases and increases their cellular uptake. Pharma. Res. 1994; 11(9): 1370-8.
Chen et al., Ionic strength-dependent persistence lengths of single-stranded RNA and DNA. Proc Natl Acad Sci USA. 2012;109:799-804.
Chen et al., Kinetics and thermodynamics of DNA hybridization on gold nanoparticles. Nucleic Acids Res. 2009;37(11):3756-3765. doi:10.1093/nar/gkp230.
Chen et al., MDR1 activation is the predominant resistance mechanism selected by vinblastine in MES-SA cells. Br. J. Cancer. 2000;83(7):892-8.
Chen et al., Nanoparticle-aptamer: an effective growth inhibitor for human cancer cells. IMECE 2009-11966. Jul. 8, 2010;271-2. https://doi.org/10.1115/IMECE2009-11966. 2 pgs.
Cheng et al., Synthesis of linear, beta-cyclodextrin-based polymers and their camptothecin conjugates. Bioconjug Chem. 2003;14:1007-1017.
Cheng et al., Tandem synthesis of core-shell brush copolymers and their transformation to peripherally cross-linked and hollowed nanostructures. J. Am. Chem. Soc. 2006;128(21):6808-9.
Cheung et al., Akt3 and mutant V600E B-Raf cooperate to promote early melanoma development. Cancer Res. 2008;68:3429-39.
Chinen et al., Spherical nucleic acid nanoparticle conjugates enhance G-quadruplex formation and increase serum protein interactions. Angew Chem Int Ed Engl. Jan. 7, 2015;54(2):527-31. doi: 10.1002/anie.201409211. Epub Nov. 13, 2014.

(56) References Cited

OTHER PUBLICATIONS

Chirila et al., The use of synthetic polymers for delivery of therapeutic antisense oligodeoxynucleotides. Biomaterials. 2002;23: 321-42.

Chithrani et al., Determining the size and shape dependence of gold nanoparticle uptake into mammalian cells. Nano Lett. 2006;6(4):662-8.

Chithrani et al., Elucidating the mechanism of cellular uptake and removal of protein-coated gold nanoparticles of different sizes and shapes. Nano Lett. 2007;7: 1542-50.

Cho et al., Immunostimulatory DNA-based vaccines induce cytotoxic lymphocyte activity by a T-helper cell-independent mechanism. Nature Biotechnol. May 2000;18:509-514.

Choi et al., DNA aptamer-passivated nanocrystal synthesis: a facile approach for nanoparticle-based cancer cell growth inhibition. Small. Mar. 2009;5(6):672-5. doi: 10.1002/smll.200801821.

Choi et al., Mechanism for the endocytosis of spherical nucleic acid nanoparticle conjugates, Proc. Natl. Acad. Sci. U.S.A. 2013;110:7625-7630.

Chompoosor et al., Charge dependence of ligand release and monolayer stability of gold nanoparticles by biogenic thiols. Bioconjugate Chem. 2008;19:1342-5.

Chu et al., Effects of photoactivated 5-aminolevulinic acid hexyl ester on MDR1 over-expressing human uterine sarcoma cells. Toxicol. Lett. 2008;181(1):7-12.

Chung et al., Nuclease-resistant DNA aptamer on gold nanoparticles for the simultaneous detection of Pb2+ and Hg2+ in human serum, Biosens. Bioelectron. 41 :827-32 (2013).

Combadiere et al., Particle-based vaccines for transcutaneous vaccination. Comp Immunol Microbiol Infect Dis. Mar. 2008;31(2-3):293-315. Epub Oct. 30, 2007. Review.

Concise Encyclopedia of Polymer Science and Engineering, "Polynucleotides," J. I. Kroschwitz Ed., John Wiley & Sons, pp. 858-859 (1990).

Connor et al., Gold nanoparticles are taken up by human cells but do not cause acute cytotoxicity. Small. 2005;1(3):325-7.

Cook, Medicinal chemistry of antisense oligonucleotides—future opportunities, Anti-Cancer Drug Design, 6:585-607 (1991).

Crawford et al., A novel B-RAF inhibitor blocks interleukin-8 (IL-8) synthesis in human melanoma xenografts, revealing IL-8 as a potential pharmacodynamic biomarker. Mol. Cancer Ther. 2008;7:492-9.

Crooke et al., Progress in antisense technology. Ann. Rev. Med. 2004;55: 61-95.

Cui et al., Topical immunization using nanoengineered genetic vaccines. J Control Release. May 17, 2002;81(1-2):173-84.

Curtis et al., A Morphology-Selective Copper Organosol. Angew. Chem. Int. Ed. Engl. 1988;27:1530-1533.

Cutler et al., Spherical nucleic acids. J Am Chem Soc. Jan. 25, 2012;134(3):1376-91. doi: 10.1021/ja209351u. Epub Jan. 9, 2012.

Dankort et al., A new mouse model to explore the initiation, progression, and therapy of BRAFV600E-induced lung tumors. Genes Dev. 2007;21: 379-84.

Dankort et al., Braf(V600E) cooperates with Pten loss to induce metastatic melanoma. Nat Genet. 2009;41: 544-52.

Davies et al., A novel AKT3 mutation in melanoma tumours and cell lines. Br. J. Cancer. 2008;99: 1265-8.

Deering et al., Nucleic acid vaccines: prospects for non-viral delivery of mRNA vaccines. Expert Opin Drug Deliv. Jun. 2014;11(6):885-99. doi: 10.1517/17425247.2014.901308. Epub Mar. 26, 2014. Review.

DeMesmaeker et al., Antisense oligonucleotides. Acc. Chem. Res. 1995;28(9): 366-74.

DeMesmaeker et al., Backbone modifications in oligonucleotides and peptide nucleic acid systems. Curr. Opin. Struct. Biol. 1995;5:343-55.

Deutsch et al., Synthesis of congeners and prodrugs. 3. Water-soluble prodrugs of taxol with potent antitumor activity. J. Med. Chem. 1989;32(4):788-92.

Dhar et al., Targeted single wall carbon nanotube mediated Pt(IV) prodrug delivery using folate as a homing device. J. Am. Chem. Soc. 2008;130(34): 11467-76.

Dhomen et al., BRAF signaling and targeted therapies in melanoma. Hematol. Oneal. Clin. North Am. 2009;23: 529-45, ix.

Dokka et al., Dermal delivery of topically applied oligonucleotides via follicular transport in mouse skin. J Invest Dermatol. 2005;124(5):971-975. doi: 10.1111/j.0022-202X.2005.23672.x.

Dulkeith et al., Gold nanoparticles quench fluorescence by phase induced radiative rate suppression. Nano Lett. 2005;5: 585-9.

Durand et al., Circular dichroism studies of an oligodeoxyribonucleotide containing a hairpin loop made of a hexaethylene glycol chain: conformation and stability. Nucl. Acids Res. 1990;18(21): 6353-9.

Dykxhoorn et al., Killing the messenger: short RNAs that silence gene expression. Nat. Rev. Mol. Cell Biol. 2003;4(6):457-67.

Eckstein, Oligonucleotides and Analogues, 1st Ed. (Oxford University Press, New York) (1991).

Elghanian et al., Selective colorimetric detection of polynucleotides based on the distancedependent optical properties of gold nanoparticles. Science. 1997;277(5329):1078-81.

Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.

Endres et al., DNA-TiO2 nanoconjugates labeled with magnetic resonance contrast agents. J. Am. Chem. Soc. 2007;129(51):15760-1 and supplementary information.

Englisch et al., "Chemically Modified Oligonucleotides as Probes and Inhibitors" Angewandte Chemie, International Edition, 30:613-629 (1991).

Enüstün et al., Coagulation of Colloidal Gold. J. Am. Chem. Soc. 1963;85:3317-3328.

Fattal et al., Biodegradable polyalkylcyanoacrylate nanoparticles for the delivery of oligonucleotides. J. Controlled Release. 1998;53:137-143.

Foldvari et al., DNA delivery for vaccination and therapeutics through the skin. Curr Drug Deliv. 2006;3(1):17-28. doi:10.2174/156720106775197493.

Freier et al., The ups and downs of nucleic acid duplex stability: structure-stability studies on chemically-modified DNA:RNA duplexes. Nucleic Acids Research. 1997;25(22):4429-4443.

Furstner et al., Catalytic carbophilic activation: catalysis by platinum and gold pi acids. Angew Chem Int Ed Engl.. 2007;46(19):3410-49.

Gao et al., Secondary structure effects on DNA hybridization kinetics: a solution versus surface comparison. Nucl. Acids Res. 2006;34: 3370-7.

Gavrieli et al., Identification of programmed cell death in situ via specific labeling of nuclear DNA fragmentation J. Cell Biol. 1992; 119(3):493-501.

Ghosh et al., Gold nanoparticles in delivery applications. Adv. Drug Deliv. Rev. 2008;60(11):1307-15.

Gibson et al., Paclitaxel-functionalized gold nanoparticles. J. Am. Chem. Soc. 2007;129(37):11653-61.

Gigler et al., "DNA-controlled assembly of a NaTl lattice structure from gold and protein nanoparticles," Nat Mater 9(11): 918-922 (2010).

Goel et al., Melanocytic nevus-like hyperplasia and melanoma in transgenic BRAFV600E mice. Oncogene. 2009;28: 2289-98.

Goodrich et al., Non-coding-RNA regulators of RNA polymerase II transcription. Nat. Rev. Mol. Cell Biol. 2006;7(8):612-6.

Gramzinski et al., Interleukin-12 and gamma interferon-dependent protection against malaria conferred by CpG oligodeoxynucleotide in mice. Infection and Immunity. Mar. 2001:1643-9.

Greish, Enhanced permeability and retention (EPR) effect for anti-cancer nanomedicine drug targeting, Methods Mal. Biol. 624:25-37 (2010).

Guo et al., CELL-SELEX: Novel perspectives of aptamer-based therapeutics. Int. J. Mol. Sci. 2008;9: 668-78.

Guy RH. Transdermal drug delivery. Handb Exp Pharmacol. 2010;(197):399-410. doi:10.1007/978-3-642-00477-3_13.

(56) References Cited

OTHER PUBLICATIONS

Halo et al., NanoFlares for the detection, isolation, and culture of live tumor cells from human blood. Proc Natl Acad Sci U S A. Dec. 2, 2014;111(48):17104-9. doi: 10.1073/pnas.1418637111. Epub Nov. 17, 2014.

Hamilton et al., A species of small antisense RNA in post-transcriptional gene silencing in plants. Science. 1999;286: 950-2.

Hammond et al., An RNA-directed nuclease mediates post-transcriptional gene silencing in *Drosophilia* cells. Nature. 2000;404: 293-6.

Han et al., A gold nanoparticle based approach for screening triplex DNA binders. J. Am. Chem. Soc. 2006;128(15):4954-5.

Hashmi et al., Gold catalysis. Angew Chem Int Ed Engl. 2006;45(47):7896-936.

Hashmi et al., Gold-catalyzed organic reactions. Chem. Rev. 2007;107:3180-211.

Hayashi, Ultrafine particles. J. Vac. Sci. Technol. 1987;5(4):1375-1384.

Hayashi, Ultrafine Particles. Physics Today. Dec. 1, 1987; 40(12): 44-60.

Hayat, (Ed.) Colloidal Gold: Principles, Methods, and Applications, vol. 1, Table of Contents, pp. v-xvii; vol. 2, Table of Contents pp. v-xix; vol. 3, Table of Contents, pp. v-xiv, Academic Press, San Diego (1989-1991).

Hellstrom et al., Epitaxial growth of DNA-assembled nanoparticle superlattices on patterned substrates. Nano Lett. 2013;13(12):6084-90. doi: 10.1021/n14033654. Epub Nov. 20, 2013.

Henglein et al., Absorption Spectrum and Some Chemical Reactions of Colloidal Platinum in Aqueous Solution. J. Phys. Chem. 1995;99:14129-14136.

Henglein, "Small-Particle Research: Physicochemical Properties of Extremely Small Colloidal Metal and Semiconductor Particles," Chem. Rev., 89:1861-1873 (1989).

Henglein, Mechanism of Reactions on Colloidal Microelectrodes and Size Quantization Effects. Top. Curr. Chem. 1988;143:113-180.

Hill et al., "Controlling the Lattice Parameters of Gold Nanoparticle FCC Crystals with Duplex DNA Linkers," Nano Lett 8(8): 2341-2344 (2008).

Holen et al., Positional effects of short interfering RNAs targeting the human coagulation trigger tissue factor. Nucl. Acids Res. 2002;30: 1757-66.

Hotz et al., VEGF antisense therapy inhibits tumor growth and improves survival in experimental pancreatic cancer. Surgery. Feb. 2005;137(2):192-9.

Hu et al., Hollow chitosan/poly(acrylic acid) nanospheres as drug carriers. Biomacromolecules. 2007;8(4):1069-76.

Hurst et al., Multisegmented one-dimensional nanorods prepared by hard-template synthetic methods. Angew. Chem. Int. Ed. Engl. 2006;45:2672-2692.

Hussain et al., A novel anionic dendrimer for improved cellular delivery of antisense oligonucleotides. J. Controlled Rei. 2004;99: 139-55.

Huxley et al., Preferential Staining of Nucleic Acid-Containing Structures for Electron Microscopy. J Biophys Biochem Cytol 1961;11:273-296 (1961).

Hwu et al., Targeted Paclitaxel by conjugation to iron oxide and gold nanoparticles. J. Am. Chem. Soc.. 2009;131(1):66-8.

Jackson et al., How do microRNAs regulate gene expression? Sci STKE. 2007(367):re1.

Jahn et al., Microfluidic directed formation of liposomes of controlled size. Langmuir. May 22, 2007;23(11):6289-93; Epub Apr. 24, 2007.

Jain et al., Synthesis of protein-loaded hydrogel particles in an aqueous two-phase system for coincident antigen and CpG oligonucleotide delivery to antigen-presenting cells. Biomacromolecules. Sep.-Oct 2005;6(5):2590-600.

Jason et al., Toxicology of antisense therapeutics. Toxicol. Appl. Pharmacol. 2004;201(1): 66-83.

Jen et al., A nonviral transfection approach in vitro: the design of a gold nanoparticle vector joint with microelectromechanical systems. Langmuir. 2004;20(4): 1369-74.

Jensen et al., Spherical nucleic acid nanoparticle conjugates as an RNAi-based therapy for glioblastoma, Sci. Trans. Med., 5:209ra152 (2013).

Jeong et al., Novel intracellular delivery system of antisense oligonucleotide by self-assembled hybrid micelles composed of DNA/PEG conjugate and cationic fusogenic peptide. Bioconjugate Chem. 2003; 14: 473-9.

Jin et al., Radiosensitization of paclitaxel, etanidazole and paclitaxel+etanidazole nanoparticles on hypoxic human tumor cells in vitro. Biomaterials. 2007;28(25):3724-30.

Jin et al., What controls the melting properties of DNA-linked gold nanoparticle assemblies? J. Am. Chem. Soc. 2003;125: 1643.

Kan et al., Distribution and effect of iodized poppyseed oil in the liver after hepatic artery embolization: experimental study in several animal species. Radiology. 1993;186(3):861-6.

Kan et al., Role of Kupffer cells in iodized oil embolization. Invest. Radiol. 1994;29(11):990-3.

Kasuya et al., Chapter 8—Bio-nanocapsule-liposome conjugates for in vivo pinpoint drug and gene delivery. Methods Enzymol. 2009;464:147-66.

Katz et al., Integrated nanoparticle-biomolecule hybrid systems: synthesis, properties, and applications. Angew. Chem. Int. Ed. 2004;43: 6042-108.

Katz, The reversible reaction of sodium thymonucleate and mercuric chloride. J. Am. Chem. Soc. 1951;74:2238-2245.

Khatri et al., Prostate-specific antigen (PSA) blood test. WebMD. Oct. 20, 2016. Accessed via https://www.webmd.com/prostate-cancer/guide/psa#1.

Kim et al., Direct synthesis of polymer nanocapsules with a noncovalently tailorable surface. Angew. Chem. Int. Ed. Engl. 2007;46(19):3471-4.

Kim et al., Direct synthesis of polymer nanocapsules: self-assembly of polymer hollow spheres through irreversible covalent bond formation. J. Am. Chem. Soc. 2010;132(28):9908-19.

Kim et al., Facile, template-free synthesis of stimuli-responsive polymer nanocapsules for targeted drug delivery. Angew. Chem. Int. Ed. Engl. 2010;49(26):4405-8.

Kimura-Suda et al., Base-Dependent Competive Adsorption of Single-Stranded DNA on Gold. Journal of the American Chemical Society. 2003; 125: 9014-9015.

Kloosterman et al., In situ detection of miRNAs in animal embryos using LNA-modified oligonucleotide probes. Nat. Methods. 2006;3: 27-9.

Kolarova et al., Preparation of magnetic oligo (dT) particles. Biotechniques. 1996;20: 196-8.

Kosturko et al., The Crystal and Molecular Structure of a 2:1 Complex of 1-Methylthymine-Mercury(1 I). Biochemistry. 1974;13:3949-3952.

Krieg, Toll-like receptor 9 (TLR9) agonists in the treatment of cancer.; Oncogene. Jan. 7, 2008;27(2):161-7. doi: 10.1038/sj.onc. 1210911.

Krutzfeldt et al., Silencing of microRNAs in vivo with 'antagomirs'. Nature. 2005;438(7068):685-9.

Kukowska-Latallo et al., Efficient transfer of genetic material into mammalian cells using Starburst polyamidoamine dendrimers. Proc. Natl. Acad. Sci. USA 1996;93:4897-4902.

Leachman et al., Therapeutic siRNAs for dominant genetic skin disorders including pachyonychia congenita. J Dermatol Sci. 2008;51(3):151-157. doi:10.1016/j.jdermsci.2008.04.003.

Lebedeva et al., Antisense oligonucleotides: Promise and reality. Annu. Rev. Pharmacol. Toxicol. 2001;41: 403-19.

Lee et al., A DNA-Gold Nanoparticle-Based Colormetric Competition Assay for the Detection of Cysteine. Nano Letter. 2008;8(2):529-533.

Lee et al., Chip-based scanometric detection of mercuric ion using DNA-functionalized gold nanoparticles. Anal. Chem. 2008;80(17):6805-8.

Lee et al., Colorimetric detection of mercuric ion (Hg2+) in aqueous media using DNA-functionalized gold nanoparticles. Angew Chem Int Ed Engl. 2007;46(22):4093-6.

(56) References Cited

OTHER PUBLICATIONS

Leslie et al., A new tool for oligonucleotides import into cells. Clin. Chem. 009;55: 609-10.

Li et al., Dual-reactive surfactant used for synthesis of functional nanocapsules in miniemulsion. J. Am. Chem. Soc. 2010;132(23):7823-5.

Li et al., Nucleolin-targeting liposomes guided by aptamer AS1411 for the delivery of siRNA for the treatment of malignant melanomas. Biomaterials. Apr. 2014;35(12):3840-50. doi: 10.1016/j.biomaterials.2014.01.019. Epub Jan. 31, 2014.

Li et al., Targeted delivery of antisense oligodeoxynucleotide and small interference RNA into lung cancer cells. Mol Pharm. Sep.-Oct 2006;3(5):579-88. doi: 10.1021/mp060039w. Publication Date:Jul. 12, 2006.

Lin et al., Effector/memory but not naive regulatory T cells are responsible for the loss of concomitant tumor immunity. J. Immunol. 2009; 182: 6095-104.

Lin et al., Modeling genomic diversity and tumor dependency in malignant melanoma. Cancer Res. 2003 ;68: 664-73.

Liu et al., Accelerated color change of gold nanoparticles assembled by DNAzymes for simple and fast colorimetric Pb2+ detection. J. Am. Chem. Soc. 2004;126: 12298-305.

Liu et al., Argonaute2 is the catalytic engine of mammalian RNAi. Science. 2004;305(5689): 1437-41.

Liu et al., Cross-linked polynorbornene-coated gold nanoparticles: dependence of particle stability on cross-linking position and cross-linker structure. Langmuir. 2008;24:11169-74.

Liu et al., De-N-acetyl GM3 promotes melanoma cell migration and invasion through urokinase plasminogen activator receptor signaling-dependent MMP-2 activation. Cancer Res. 2009;69: 8662-9.

Liu et al., New Poly(D-glucaramidoamine)s Induce DNA Nanoparticle Formation and Efficient Gene Delivery into Mammalian Cells. J. Am. Chem. Soc. 2004;126:7422-7423.

Liu et al., Synthesis, stability, and cellular internalization of gold nanoparticles containing mixed peptide-poly( ethylene glycol) monolayers. Anal. Chem. 2007;79: 2221-9.

Liubimova et al., Nanoconjugate based on polymalic acid for tumor targeting. Chem Biol Interact. Jan. 30, 2008;171(2):195-203. Epub Feb. 8, 2007.

Llovet et al., Arterial embolisation or chemoembolisation versus symptomatic treatment in patients with unresectable hepatocellular carcinoma: a randomised controlled trial. Lancet. 2002;359(9319):1734-9.

Lohcharoenkal et al., Protein Nanoparticles as Drug Delivery Carriers for Cancer Therapy. BioMed Research International. 2014; Article ID 180549. 12 pages. http://dx.doi.org/10.1155/2014/180549.

Love et al., Self-assembled monolayers of thiolates on metals as a form of nanotechnology. Chem. Rev. 2005; 105: 1103-69.

Luo et al., Synthetic DNA delivery systems. Nat Biotechnol. Jan. 2000;18(1):33-7.

Lytton-Iean et al., A thermodynamic investigation into the binding properties of DNA functionalized gold nanoparticle probes and molecular fluorophore probes. J Am Chem Soc. Sep. 21, 2005;127(37):12754-5.

Ma et al., Design and synthesis of RNA miniduplexes via a synthetic linker approach. 2. Generation of covalently closed, double-stranded cyclic HIV-1 TAR RNA analogs with high Tat-binding affinity. Nucl. Acids Res. 1993;21: 2585-9.

Ma et al., Design and synthesis of RNA miniduplexes via a synthetic linker approach. Biochemistry. 1993;32(7): 1751-8.

Marinakos et al., Gold Nanoparticles as Templates for the Synthesis of Hollow Nanometer-Sized Conductive Polymer Capsules. Adv. Mater. 1999;11: 34-37.

Marinakos et al., Template Synthesis of One-Dimensional Au, Au-Poly(pyrrole), and Poly(pyrrole) Nanoparticle Arrays. Chem. Mater. 1998;10:1214-19.

Marunson et al., Impact of Class A, B and C CpG-oligodeoxynucleotides on in vitro activation of innate immune cells in human immunodeficiency virus-1 infected individuals. Immunology. 2007;120(4):526-35.

Maruyama, et al., Nanoparticle DNA carrier with poly(L-lysine) grafted polysaccharide copolymer and poly(D,L-lactic acid). Bioconjugate Chem.. 1997;8: 735-742.

Massart, Preparation of aqueous magnetic liquids in alkaline and acidic media. IEEE Transactions on Magnetics. 1981;17(2): 1247-8.

Matijevic et al., Fine Particles Part II: Formation Mechanisms and Applications. MRS Bulletin pp. 16-47 (1990).

Maxwell et al., Self-assembled nanoparticle probes for recognition and detection of biomolecules. J. Am. Chem. Soc. 2002;124: 9606-12.

Maye et al., A simple method for kinetic control of DNA-induced nanoparticle assembly. J. Am. Chem. Soc. 2006; 128: 14020-1.

Mckenzie et al., Sequence-specific DNA detection using high-affinity LNA-functionalized gold nanoparticles. Small. Nov. 2007;3(11):1866-8.

McManus et al., Gene silencing in mammals by small interfering RNAs. Nat. Rev. Genet. 2002;3(10): 737-47.

Mendell, MicroRNAs: critical regulators of development, cellular physiology and malignancy. Cell Cycle. 2005 ;4(9):1179-84.

Miller et al., Antisense oligonucleotides: Strategies for delivery. PSTT. 1998; 1(9): 377-86.

Ming et al., Albumin-based nanoconjugates for targeted delivery of ; therapeutic oligonucleotides. Biomaterials. Oct. 2013;34(32):7939-49. doi: 10.1016/j.biomaterials.2013.06.066. Epub Jul. 19, 2013.

Mittal, Improving the efficiency of RNA interference in mammals. Nat. Rev. Genet. 2004;5(5):355-65.

Mohamed et al., TLR9 mediates *S. aureus* killing inside osteoblasts via induction of oxidative stress. BMC Microbiol. Oct. 3, 2016;16(1):230.

Nykypanchuk et al., DNA-guided crystallization of colloidal nanoparticles. Nature. 2008;451: 549-52.

Ohishi et al., Hepatocellular carcinoma detected by iodized oil. Use of anticancer agents. Radiology. 1985;154(1):25-9.

Okayasu et al., Selective and persistent deposition and gradual drainage of iodized oil, Lipiodol in the hepatocellular carcinoma after injection into the feeding hepatic artery. Am. J. Clin. Pathol. 1988;90(5):536-44.

Olshavsky et al., Organometallic Synthesis of GaAs Crystallites Exhibiting Quantum Confinement. J. Am. Chem. Soc. 1990;112, 9438-9439.

O'Meara et al., Capture of single-stranded DNA assisted by oligo-nucleotide modules. Anal. Biochem. 1998;255: 195-203.

Opalinska et al., Nucleic-acid therapeutics: basic principles and recent applications. Nat Rev Drug Discov. Jul. 2002;1(7):503-14.

Ozpolat et al., Nanomedicine based approaches for the delivery of siRNA in cancer. J. Intern. Med. 2010;267(1):44-53.

Paciotti et al., Colloidal gold: a novel nanoparticle vector for tumor directed drug delivery. Drug Deliv. 2004;11(3):169-83.

Parrish et al., Functional anatomy of a dsRNA trigger: Differential requirement for the two trigger strands in RNA interference. Mol. Cell. 2000;6: 1077-87.

Patil et al., DNA-based therapeutics and DNA delivery systems: a comprehensive review. AAPS J., 2005;7(1): E61-77.

Patil et al., Temozolomide delivery to tumor cells by a multifunctional nano vehicle based on poly(-L-malic acid). Pharm Res. Nov. 2010;27(11):2317-29. doi: 10.1007/s11095-010-0091-0. Epub Apr. 13, 2010.

Platt al., Role for the class A macrophage scavenger receptor in the phagocytosis of apoptotic thymocytes in vitro. Proc Natl Acad Sci U S A. Oct. 29, 1996;93(22):12456-60.

Prasad et al., Oligonucleotides tethered to a short polyguanylic acid stretch are targeted to macrophages: enhanced antiviral activity of a vesicular stomatitis virus-specific antisense oligonucleotide. Antimicrob Agents Chemother. Nov. 1999;43(11):2689-96.

Prigodich et al., Multiplexed nanoflares: mRNA detection in live cells. Anal Chem. Feb. 2012; 21;84(4):2062-6. doi: 10.1021/ac202648w. Epub Jan. 30, 2012.

(56) References Cited

OTHER PUBLICATIONS

Radovic-Moreno et al., Immunomodulatory spherical nucleic acids. Proc Natl Acad Sci U S A. Mar. 31, 2015;112(13):3892-7. doi: 10.1073/pnas.1502850112. Epub Mar. 16, 2015.
Raj et al., Stochastic mRNA synthesis in mammalian cells. PLoS Biol., 2006;4(10): e309.
Rethore et al., Preparation of chitosan/polyglutamic acid spheres based on the use of polystyrene template as nonviral gene carrier. Tissue Engineering, 2009;15(4): 605-13.
Rethore et al., Use of templates to fabricate nanoscale spherical structures for defined architectural control. Small, 2010;6(4):488-98.
Rihova et al., Receptor-mediated targeted drug or toxin delivery. Adv. Drug Deliv. Rev., 1998;29(3): 273-89.
Sadauskas et al., Protracted elimination of gold nanoparticles from mouse liver, Nanomedicine, 2009;5(2):162-9.
Sambrook et al., Molecular Cloning: A Laboratory Manual 2nd ed. (1989). Table of contents only.
Sanghvi, Chapter 15, Antisense Research and Application, Ed. S. T. Crooke and B. Lebleu, CRC Press, (1993).
Schifferlers et al., Cancer siRNA therapy by tumor selective delivery with ligand-targeted sterically stabilized nanoparticle. Nucl. Acid Res., 2004;32(19): e149.
Schmid, G. (ed.) Clusters and Colloids (VCH, Weinheim) (1994). Table of contents only.
Sharma et al., Mutant V599EB-Raf regulates growth and vascular development of malignant melanoma tumors. Cancer Res., 2005;65: 2412-21.
Sharma et al., Targeting Akt3 signaling in malignant melanoma using isoselenocyanates. Clin. Cancer Res., 2009; 15:.1674-85.
Sharma et al., Targeting mitogen-activated protein kinase/extracellular signal-regulated kinase kinase in the mutant (V600E) B-Raf signaling cascade effectively inhibits melanoma lung metastases. Cancer Res., 2006;66: 8200-9.
Sharp et al., RNA interference—2001. Genes Dev., 2001;15: 485-90.
Shu et al., Gradient cross-linked biodegradable polyelectrolyte nanocapsules for intracellular protein drug delivery. Biomaterials, 2010;31 (23):6039-49.
Shukla et al., Development of streptavidin-based ; nanocomplex for siRNA delivery. Mol Pharm. Dec. 2, 2013;10(12):4534-45. doi:; 10.1021/mp400355q. Epub Oct. 25, 2013.
Skwarczynski et al., Paclitaxel prodrugs: toward smarter delivery of anticancer agents. J. Med. Chem. 2006;49(25):7253-69.
Smith et al., Bioconjugated quantum dots for in vivo molecular and cellular imaging. Adv. Drug Deliv. Rev., 2008;60(11):1226-40.
Sokol et al., Real time detection of DNA.RNA hybridization in living cells. Proc. Natl. Acad. Sci. USA, 1998;95: 11538-43.
Stahl et al., Deregulated Akt3 activity promotes development of malignant melanoma. Cancer Res., 2004;64: 7002-10.
Stoeva et al., Multiplexed detection of protein cancer markers with biobarcoded nanoparticle probes. J. Am. Chem. Soc., 2006;128: 8378-9.
Storz et al., An abundance of RNA regulators. Annu. Rev. Biochem., 2005;74:199-217.
Sugihara et al., One-pot synthesis of biomimetic shell cross-linked micelles and nanocages by ATRP in alcohol/water mixtures. Angew. Chem. Int. Ed. Engl., 2010;48(20):3500-3.
Tan et al., Facile synthesis of hybrid silica nanocapsules by interfacial templating condensation and their application in fluorescence imaging. Chem. Commun. (Camb.), Nov. 2009; 7(41):6240-2.
Taton et al., Scanometric DNA array detection with nanoparticle probes. Science, 2000;289(5485):1757-60.
Thomas et al., Conjugation to gold nanoparticles enhances polyethylenimine's transfer of plasmid DNA into mammalian cells. Proc. Natl. Acad. Sci. USA, 2003;100(16): 9138-43.
Thomas, The Interaction of HgCl2 with Sodium Thymonucleate. J. Am. Chem. Soc., 1954;76:6032-6034.
Thurn et al., Labeling TiO2 nanoparticles with dyes for optical fluorescence microscopy and determination of TiO2-DNA nanoconjuqate stability. Small, 2009;5(11):1318-25.
Tondelli, et al., Highly efficient cellular uptake of c-myb antisense oligonucleotides through specifically designed polymeric nanospheres. Nucl. Acids Res. 1998;26:5425-5431.
Tsao et al., Genetic interaction between NRAS and BRAF mutations and PTEN/MMAC1 inactivation in melanoma. J. Invest. Dermatol., 2004;122: 337-41.
Uchida et al., GaAs Nanocrystals Prepared in Quinoline. J. Phys. Chem., 1992;95, 5382-5384.
Virmani et al., Comparison of two different methods for inoculating VX2 tumors in rabbit livers and hind limbs. J. Vasc. Interv. Radial., 2008;19(6):931-6.
Wagner et al., Gene inhibition using antisense oligodeoxynucleotides. Nature, 1994;372: 333-5.
Wang et al., Co-delivery of drugs and DNA from cationic core-shell nanoparticles selfassembled from a biodegradable copolymer. Nat Mater. Oct. 2006;5(10):791-6. doi: 10.1038/nmat1737. Epub Sep. 24, 2006. PMID: 16998471.
Wang et al., Nanometer-Sized Semiconductor Clusters: Materials Synthesis, Quantum Size Effects, and Photophysical Properties. J. Phys. Chem., 1991;95:525-532.
Wang et al., Nanoparticles for multiplex diagnostics and imaging. Nanomedicine (Land.), 2006;1: 413-26.
Wang et al., Superparamagnetic sub-5 nm Fe@C nanoparticles: isolation, structure, magnetic properties, and directed assembly. Nano Lett., 2008;8(11):3761-5.
Wellbrock et al., V599EB-RAF is an oncogene in melanocytes. Cancer Res., 2004;64: 2338-42.
Weller, Colloidal Semiconductor Q-Particles: Chemistry in the Transition Region Between Solid State and Molecules. Angew. Chem. Int. Ed. Engl., 1993;32:41-53.
Wolf et al., Rapid hybridization kinetics of DNA attached to submicron latex particles. Nucl. Acids Res., 1987;15:2911-26.
Wu et al., Intracellular fate of spherical nucleic acid nanoparticle conjugates. J Am Chem Soc. May 28, 2014;136(21):7726-33. doi: 10.1021/ja503010a. Epub May 19, 2014.
Xu et al., A gold-nanoparticle-based real-time colorimetric screening method for endonuclease activity and inhibition. Angew. Chem. Int. Ed. Engl., 2007;46(19):3468-70.
Xu et al., Homogeneous detection of nucleic acids based upon the light scattering properties of silver-coated nanoparticle probes. Anal. Chem., 2007;79(17):6650-4.
Xu et al., Thermodynamics of DNA hybridization on gold nanoparticles. J. Am. Chem. Soc., 2005;127(38): 13227-31.
Yamane et al., On the complexing of desoxyribonucleic acid (DNA) by mercuric ion. J. Am. Chem. Soc., 1961;83:2599-2607.
Yang et al., Evidence that processed small dsRNAs may mediate sequence-specific mRNA degradation during RNAi in *Drosophila* embryos. Curr. Biol., 2000;10: 1191-200.
Yin Win et al., Effects of particle size and surface coating on cellular uptake of polymeric nonparticles for oral delivery of anticancer drugs. Biomaterials, 2005;26: 2713-22.
Zabner et al., Cellular and molecular barriers to gene transfer by a cationic lipid. J. Biol. Chem., 1995;270: 18997-9007.
Zamai et al., Camptothecin Poly[N-(2-Hydroxypropyl) Methacrylamide] Copolymers in Antitopoisomerase-1 Tumor Therapy: Intratumor Release and Antitumor Efficacy. Mol Cancer Ther 2003;2: 29-40.
Zamore et al., RNAi: Double-Stranded RNA Directs the ATP-Dependent Cleavage of mRNA at 21 to 23 Nucleotide Intervals. Cell. 2000;101:25-33.
Zhang et al., An extremely stable and orthogonal DNA base pair with a simplified three-carbon backbone. J. Am. Chem. Soc., 2005;127:74-75.
Zhang et al., Cationic shell-crosslinked knedel-like nanoparticles for highly efficient gene and oligonucleotide transfection of mammalian cells. Biomaterials, 2009;30(5):968-77.
Zhang et al., Single-quantum-dot-based DNA sensor. Nat. Mater., 2005;4: 826-31.

(56) References Cited

OTHER PUBLICATIONS

Zhang et al., TLR9-mediated siRNA delivery for targeting of normal and malignant human hematopoietic cells in vivo. Blood. Feb. 21, 2013;121(8):1304-15. doi: 10.1182/blood-2012-07-442590. Epub Jan. 3, 2013.

Zhao et al., A rapid bioassay for single bacterial cell quantitation using bioconjugated nanoparticles. Proc. Natl. Acad. Sci. USA, 2004;101(42):15027-32.

Zheng et al., Aptamer nano-flares for molecular detection in living cells, Nano Lett., 9: 3258 (2009).

Zheng et al., Sterically controlled docking of gold nanoparticles on ferritin; surface by DNA hybridization. Nanotechnology. Jul. 8, 2011;22(27):275312. doi:; 10.1088/0957-4484/22/27/275312. Epub May 26, 2011.

Zimmer, Antisense oligonucleotide delivery with polyhexylcyanoacrylate nanoparticles as carriers. Methods, 1999; 18: 286-95.

Zimmermann, et al., A Novel Silver(1)-Mediated DNA Base Pair. J. Am. Chem. Soc., 2002;124:13684-13685.

Bozzuto et al., Liposomes as nanomedical devices. Int J Nanomedicine. Feb. 2, 2015;10:975-99. doi: 10.2147/IJN.S68861.

Chandaroy et al., Temperature-controlled content release from liposomes encapsulating Pluronic F127. J Control Release. Sep. 11, 2001;76(1-2):27-37. doi: 10.1016/s0168-3659(01)00429-1.

Chen et al., Oncology Meets Immunology: The Cancer-Immunity (2013) Cycle Immunity 39(1):1-10. https://doi.org/10.1016/j.immuni.2013.07.012.

He et al., Anticancer effects of combinational treatment with BRAFV600E siRNA and PI3K pathway inhibitors in melanoma cell lines harboring BRAFV600E. Oncol Lett. 2018;16(1):632-642. Epub May 2, 2018. doi:10.3892/ol.2018.8614.

Hofmann et al., Phase 1 Evaluation of Intralesionally Injected TLR9-agonist PF-3512676 in Patients With Basal Cell Carcinoma or Metastatic Melanoma, Journal of Immunotherapy: Jun. 2008—vol. 31—Issue 5—p. 520-527 doi: 10.1097/CJI.0b013e318174a4df.

Karami et al., Liposomes as a novel drug delivery system: fundamental and pharmaceutical application. Asian J Pharm. Jan.-Mar. 2018 (Suppl);12(1):S31.

Kim et al., Systemic and Specific Delivery of Small Interfering RNAs to the Liver Mediated by Apolipoprotein A-I. Mol. Ther., 2007, 15 (6), 1145-1152.

Migden et al., PD-1 Blockade with Cemiplimab in Advanced Cutaneous Squamous-Cell Carcinoma. N Engl J Med. 2018;379(4):341-351. doi:10.1056/NEJMoa1805131.

Millward et al. Phase I study of tremelimumab (CP-675 206) plus PF-3512676 (CPG 7909) in patients with melanoma or advanced solid tumours. Br J Cancer 108, 1998-2004 (2013). https://doi.org/10.1038/bjc.2013.227.

Munhoz et al., Clinical Development of PD-1 in Advanced Melanoma. Cancer J. 2018;24(1):7-14. doi:10.1097/PPO.0000000000000299. Author Manuscript, 17 pages.

Nemati et al., Using siRNA-based spherical nucleic acid nanoparticle conjugates for gene regulation in psoriasis. J Control Release. Dec. 28, 2017;268:259-268. doi: 10.1016/j.jconrel.2017.10.034. Epub Oct. 23, 2017.

Shahzad et al., Targeted delivery of small interfering RNA using reconstituted high-density lipoprotein nanoparticles. Neoplasia. Apr. 2011;13(4):309-19.

Tran et al., Targeting V600EB-Raf and Akt3 using nanoliposomal-small interfering RNA inhibits cutaneous melanocytic lesion development. Cancer Res. Sep. 1, 20085;68(18):7638-49. doi: 10.1158/0008 -5472. C AN-07-6614.

Walter et al. Cancer-testis antigens and immunosurveillance in human cutaneous squamous cell and basal cell carcinomas. Clin Cancer Res. 2010;16(14):3562-3570. doi:10.1158/1078-0432.CCR-09-3136.

Yarchoan et al., Tumor Mutational Burden and Response Rate to PD-1 Inhibition. N Engl J Med. 2017;377(25):2500-2501. doi:10.1056/NEJMc1713444. Author Manuscript, 4 pages.

\* cited by examiner

A

B

ADOPTIVE CELL THERAPY USING SPHERICAL NUCLEIC ACIDS (SNAS)

CROSS REFERENCE TO RELATED APPLICATIONS

This application is a national stage filing under 35 U.S.C. § 371 of International Application No. PCT/US2018/032372, filed May 11, 2018, which claims the priority benefit under 35 U.S.C. § 119(e) of U.S. Provisional Application No. 62/505,092, filed May 11, 2017, the disclosure of each of which is incorporated herein by reference in their entireties.

STATEMENT OF GOVERNMENT SUPPORT

This invention was made with government support under U54 CA199091 awarded by the National Institutes of Health. The government has certain rights in the invention.

INCORPORATION BY REFERENCE OF MATERIALS SUBMITTED ELECTRONICALLY

This application contains, as a separate part of the disclosure, a Sequence Listing in computer readable form (Filename: 2017-088_Seqlisting.txt; Size: 460 bytes; Created: May 11, 2018), which is incorporated by reference in its entirety.

BACKGROUND

Spherical nucleic acid (SNA) technology has been demonstrated to be a potent gene regulation and immunostimulatory agent. Current SNA constructs are utilized to deliver therapeutic nucleic acids into the cells. SNAs are a class of nanoconjugates that are overcoming challenges that face current nucleic acid therapies. They provide privileged access at both the cellular and tissue levels. For example, SNAs are actively transported across cell membranes by engaging Class A scavenger receptors [Choi et al., Proc, Natl. Acad. Sci. USA 2013, 110, 7625; Wu et al., J. Am. Chem. Soc. 2014, 136, 7726] while unmodified linear nucleic acids do not enter cells in significant amounts without the use of transfection agents [Luo et al., Nat. Biotechnol. 2000, 18, 33; Opalinska et al., Nat. Rev. Drug Discov. 2002, 1, 503]. In addition, the polyvalent, densely functionalized nucleic acid shell that defines an SNA can act as a high affinity binder for different classes of ligands, including certain receptor proteins [Choi et al., Proc, Natl. Acad. Sci. USA 2013, 110, 7625] and complementary nucleic acid sequences [Lytton-Jean et al., J. Am. Chem. Soc. 2005, 127, 12754]. Consequently, SNAs have emerged as a powerful platform for developing molecular diagnostic probes [Halo et al., Proc. Natl. Acad. Sci. USA 2014, 111, 17104; Prigodich et al., Anal. Chem. 2012, 84, 2062; Zheng et al., Nano Lett. 2009, 9, 3258], and as lead compounds in gene regulation [Jensen et al., Sci. Transl. Med. 2013, 5, 209ra152] and immunomodulation therapies [Radovic-Moreno et al., Proc. Natl. Acad. Sci. USA 2015, 112, 3892; Banga et al., J. Am. Chem. Soc. 2017, 139, 4278]. The three-dimensional architecture of the SNA, rather than the chemical composition of the NP core, is the origin of many of the biochemical properties that make them exceedingly useful in the life sciences and medicine [Choi et al., Proc, Natl. Acad. Sci. USA 2013, 110, 7625; Cutler et al., J. Am. Chem. Soc. 2012, 134, 1376].

Cell-based therapy (e.g., cell-based immunotherapy) is a therapy with curative potential for the treatment of cancer. T cells and other immune cells may be modified to target tumor antigens through the introduction of an antigen that is specific to a tumor antigen.

SUMMARY

Disclosed herein are spherical nucleic acid (SNA) materials (i.e., structures consisting of a nanoparticle core, oligonucleotides, and other possible classes of molecule—including peptide or protein antigens) in a cell-based therapy. In some embodiments of the present disclosure, the SNAs are first used to treat a subset of cells ex vivo before reinfusion into the animal or patient; this key step allows for a controlled environment for the SNAs to interact with cells, and is advantageous compared with a system in which distribution of SNAs throughout the body occurs following injection of SNAs directly into a patient subcutaneously or intravenously via the blood stream. The types of cells contemplated by the disclosure include, but are not limited to T-cells (e.g., CD4, CD8, and gamma delta), natural killer (NK) cells, B-cells, macrophages, and dendritic cells.

In some embodiments, after the SNAs are allowed to enter and activate the cells, the SNA-loaded cells are then re-infused into animals, at which time the active agent becomes the cells themselves. These SNA-loaded cells perform multiple functions in an immunotherapeutic mode of action. Among the demonstrated activities of these cells, once re-introduced to animal models, are 1) the transfer of SNA and SNA components (adjuvant polynucleotides (e.g., a CpG oligonucleotide), antigens) to other cells (such as an antigen presenting cell (APC)); and 2) direct attack of target cells.

The method of using SNAs to enter and activate cells outside the body, as disclosed herein, enables superior activation of these cells and targeting to the tumor site and lymph system only. This avoids the potential problems of SNA distribution to non-target organs.

In various embodiments, the methods of the disclosure are used to treat cancer. In related embodiments, the cancer is a hematological tumor or a solid tumor. In still further embodiments, the cancer is bladder cancer, brain cancer, cervical cancer, colon/rectal cancer, leukemia, lymphoma, liver cancer, ovarian cancer, pancreatic cancer, sarcoma, prostate cancer, or breast cancer.

In some aspects, the disclosure provides a composition comprising a pharmaceutically acceptable carrier and a cell having a spherical nucleic acid (SNA) contained therein, wherein the cell is obtained from an individual and the SNA comprises a nanoparticle, an oligonucleotide on the surface of the nanoparticle, and an antigen. In some embodiments, the antigen is a prostate-specific antigen (PSA) peptide, mesothelin, glycoprotein 100 (gp100), prostate specific membrane antigen (PSMA), or prostatic acid phosphatase (PAP). In further embodiments, the nanoparticle is a liposome. In some embodiments, the liposome comprises a lipid selected from the group consisting of 1,2-dioleoyl-sn-glycero-3-phosphocholine (DOPC), 1,2-dimyristoyl-sn-phosphatidylcholine (DMPC), 1-palmitoyl-2-oleoyl-sn-phosphatidylcholine (POPC), 1,2-distearoyl-sn-glycero-3-phospho-(1'-rac-glycerol) (DSPG), 1,2-dioleoyl-sn-glycero-3-phospho-(1'-rac-glycerol) (DOPG), 1,2-distearoyl-sn-glycero-3-phosphocholine (DSPC), 1,2-dipalmitoyl-sn-glycero-3-phosphocholine (DPPC), 1,2-di-(9Z-octadecenoyl)-sn-glycero-3-phosphoethanolamine (DOPE), 1,2-dihexadecanoyl-sn-glycero-3-phosphoethanolamine (DPPE), cardiolipin, and lipid A.

In further embodiments, the oligonucleotide comprises a tocopherol, a cholesterol moiety, DOPE-butamide-phenyl-maleimido, or lyso-phosphoethanolamine-butamide-pneyl-maleimido. In some embodiments, the oligonucleotide comprises RNA or DNA. In still further embodiments, the oligonucleotide comprises a sequence that is a toll-like receptor (TLR) agonist. In some embodiments, the TLR is chosen from the group consisting of toll-like receptor 1 (TLR1), toll-like receptor 2 (TLR2), toll-like receptor 3 (TLR3), toll-like receptor 4 (TLR4), toll-like receptor 5 (TLR5), toll-like receptor 6 (TLR6), toll-like receptor 7 (TLR7), toll-like receptor 8 (TLR8), toll-like receptor 9 (TLR9), toll-like receptor 10 (TLR10), toll-like receptor 11 (TLR11), toll-like receptor 12 (TLR12), and toll-like receptor 13 (TLR13). In some embodiments, the oligonucleotide comprises a CpG nucleotide sequence.

In some embodiments, the composition further comprises an additional oligonucleotide. In further embodiments, the additional oligonucleotide comprises RNA or DNA. In still further embodiments, the RNA is a non-coding RNA. In some embodiments, the non-coding RNA is an inhibitory RNA (RNAi). In further embodiments, the RNAi is selected from the group consisting of a small inhibitory RNA (siRNA), a single-stranded RNA (ssRNA) that forms a triplex with double stranded DNA, and a ribozyme. In some embodiments, the RNA is a microRNA. In further embodiments, the DNA is antisense-DNA.

In some embodiments, the nanoparticle has a diameter of 50 nanometers or less. In further embodiments, the SNA comprises about 10 to about 80 double stranded oligonucleotides. In some embodiments, the SNA comprises 70 double stranded oligonucleotides.

In some embodiments, the cell is a T-cell, a natural killer (NK) cell, a B-cell, a macrophage, a dendritic cell, or a combination thereof. In further embodiments, the antigen is encapsulated in the nanoparticle. In some embodiments, the antigen is on the surface of the nanoparticle.

In some aspects, the disclosure provides a method of making a composition of the disclosure comprising contacting the cell with the SNA to form the composition. In some embodiments, the cell is obtained from an individual in need of adoptive cell therapy.

In some aspects, the disclosure provides a vaccine comprising a composition of the disclosure, and an adjuvant.

In some aspects, the disclosure provides a method of treating an individual in need of adoptive cell therapy comprising administering a composition of the disclosure to the individual.

In some aspects, a method of producing an immune response to cancer in an individual is provided, comprising administering to the individual an effective amount of a composition of the disclosure, or a vaccine of the disclosure, thereby producing an immune response to cancer in the individual. In some embodiments, the immune response is a neutralizing antibody response or a protective antibody response.

In some aspects, the disclosure provides a method of immunizing an individual against cancer comprising administering to the individual an effective amount of a composition or a vaccine of the disclosure, thereby immunizing the individual against cancer. In some embodiments, the cancer is selected from the group consisting of prostate, breast, melanoma, and lung cancer.

In some aspects, a method of inhibiting expression of a gene is provided comprising hybridizing a polynucleotide encoding the gene with one or more oligonucleotides complementary to all or a portion of the polynucleotide, the oligonucleotide being the additional oligonucleotide of a composition of the disclosure, wherein hybridizing between the polynucleotide and the oligonucleotide occurs over a length of the polynucleotide with a degree of complementarity sufficient to inhibit expression of the gene product. In some embodiments, expression of the gene product is inhibited in vivo. In further embodiments, expression of the gene product is inhibited in vitro. In still further embodiments, the gene is PD-1 or PD-L1.

DETAILED DESCRIPTION

The present disclosure is directed to compositions comprising SNAs and their use in cell-based therapies. There are several advantages to using SNAs in cell-based therapies. For example, the 3-D structure of the SNA creates a platform for vast combinations of oligonucleotide shell decoration and protein (e.g., antibodies, peptides, cytokines) encapsulation within the core. SNAs of the disclosure load material into T-cells ex vivo to create T-cell chaperones. This flexibility allows for the creation of personalized T-cell therapy via SNA design. In some embodiments, the antigen core of the SNA guides the attack against different types of cancer based on the expression of tumor associated antigens. The endocytosis of SNAs allows for non-viral modification of T-cells to create multifunctional T-cell chaperones. T-cell chaperones transfer SNA derived adjuvant and antigen cargo to APCs in vivo to boost priming function and directly kill tumor cells. T-cell chaperones efficiently home to immune priming sites, including draining lymph nodes and tumor tissue. T-chaperone bystander transfer eliminates the need for systemic administration regimens, decreases the amount of SNA material needed, and prevents off-target side effects associated with systemic drugs.

The terms "polynucleotide" and "oligonucleotide" are interchangeable as used herein.

The term "T cell chaperone" or "T chap" refers to a cell that has been contacted with a SNA of the disclosure, in order to load the cell with an immunestimulatory oligonucleotide and a tumor-associated antigen.

An "immune response" is a response of a cell of the immune system, such as a B cell, T cell, or monocyte, to a stimulus, such as a pathogen or antigen (e.g., formulated as an antigenic composition or a vaccine). An immune response can be a B cell response, which results in the production of specific antibodies, such as antigen specific neutralizing antibodies. An immune response can also be a T cell response, such as a CD4⁺ response or a CD8⁺ response. B cell and T cell responses are aspects of a "cellular" immune response. An immune response can also be a "humoral" immune response, which is mediated by antibodies. In some cases, the response is specific for a particular antigen (that is, an "antigen-specific response"). An immune response can be measured, for example, by ELISA-neutralization assay. Exposure of a subject to an immunogenic stimulus, such as an antigen (e.g., formulated as an antigenic composition or vaccine), elicits a primary immune response specific for the stimulus, that is, the exposure "primes" the immune response.

As used in this specification and the appended claims, the singular forms "a," "an," and "the" include plural reference unless the context clearly dictates otherwise.

Spherical Nucleic Acids.

Figure 1:
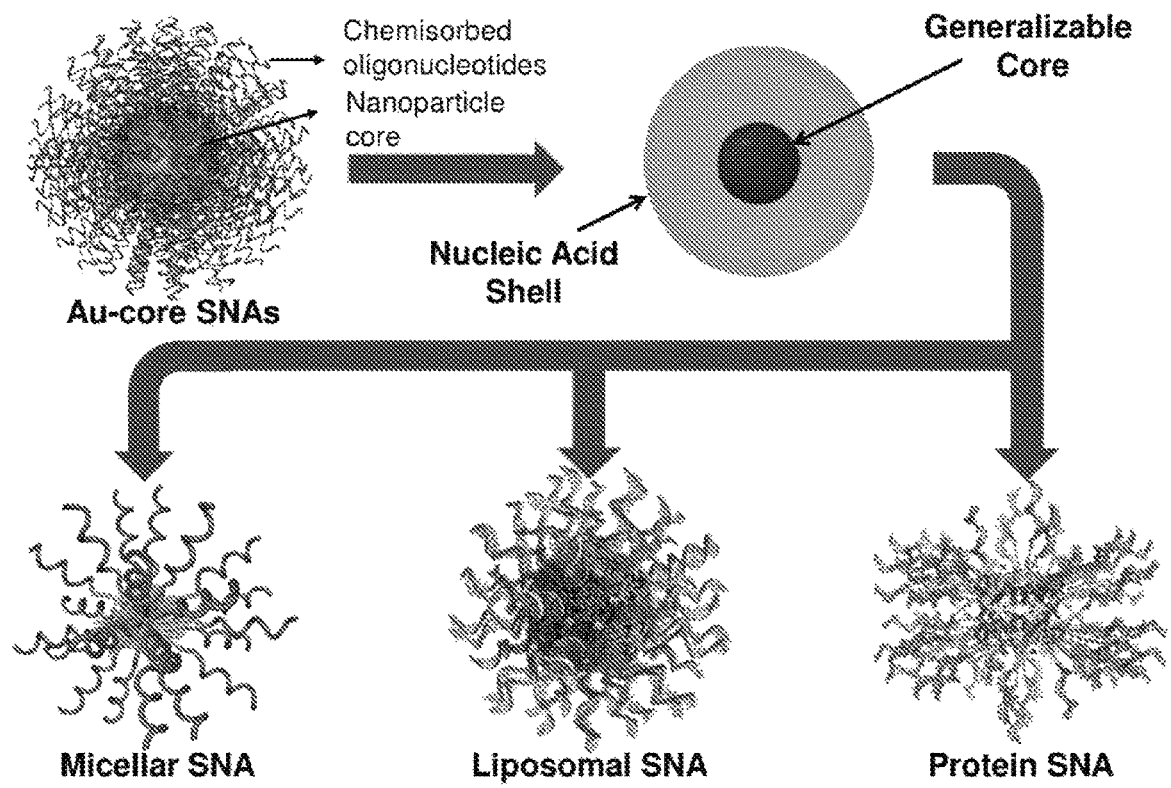
FIG. 1 depicts various SNAs, showing that the SNAs can vary both in composition and in structure.
Figure 2:
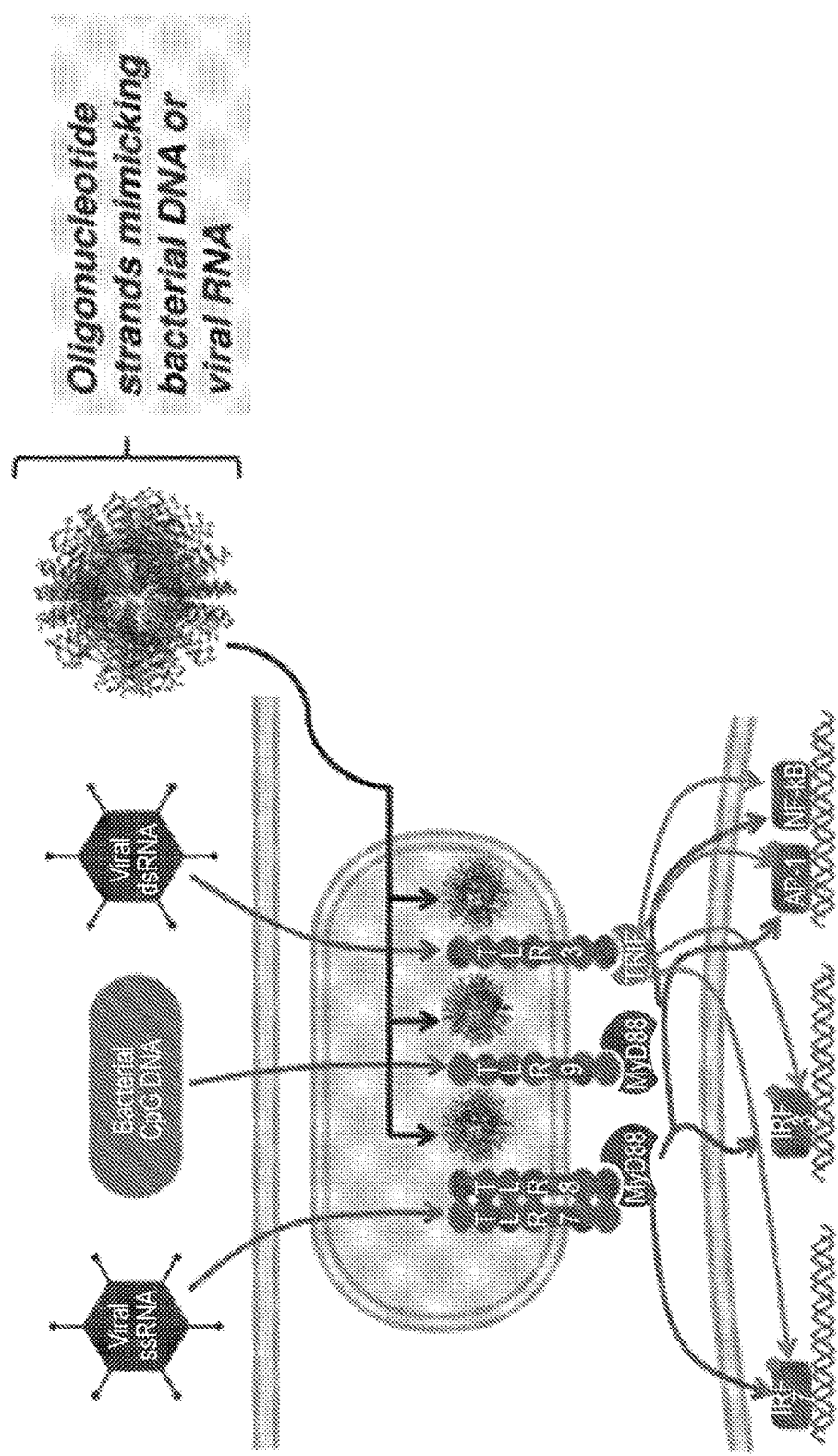
FIG. 2 is a schematic depicting the immunostimulatory effects an SNA can have following endocytosis.
Figure 3:
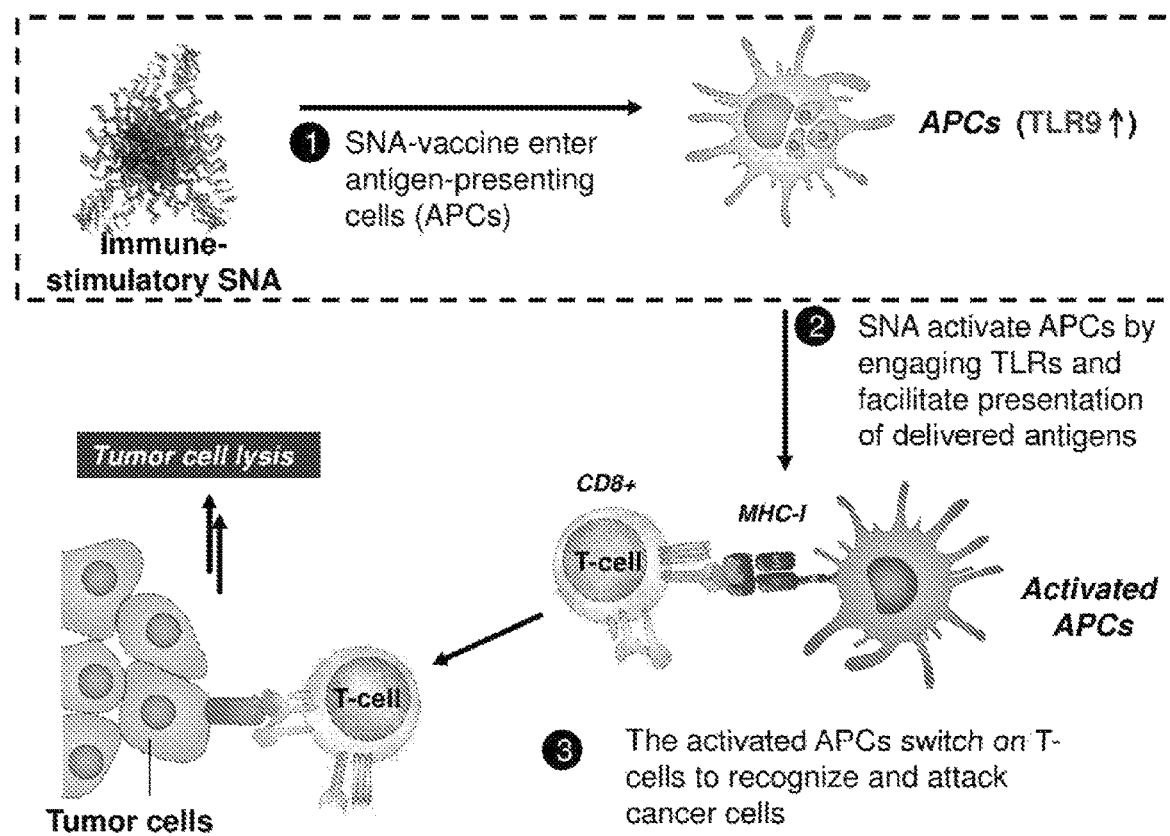
FIG. 3 is a schematic illustrating the use of SNAs as a vaccine for cancer.
Figure 4:
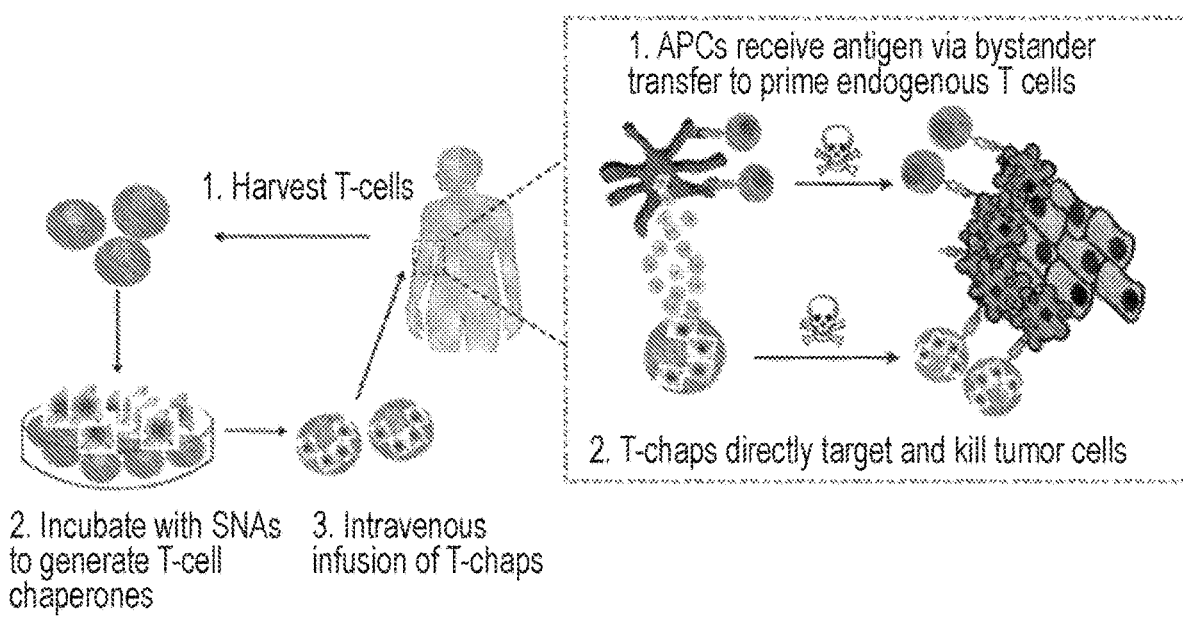
FIG. 4 is a schematic depicting the use of SNAs in T-cell chaperone cellular therapy.

Spherical nucleic acids (SNAs) comprise densely functionalized and highly oriented polynucleotides on the surface of a nanoparticle which can either be organic (e.g., a liposome) inorganic (such as gold, silver, or platinum) or hollow (e.g., silica-based). The spherical architecture of the polynucleotide shell confers unique advantages over traditional nucleic acid delivery methods, including entry into nearly all cells independent of transfection agents and resistance to nuclease degradation. Furthermore, SNAs can penetrate biological barriers, including the blood-brain and blood-tumor barriers as well as the epidermis. See FIG. 1. SNAs are useful in a myriad of biomedical applications, including as gene regulatory therapeutics (where SNAs are formulated with antisense and/or siRNA oligonucleotides) and as immunostimulatory (IS) therapeutics (where SNAs are formulated with immunostimulatory oligonucleotides and can induce an immunotherapeutic response—see FIGS. 2-4). As a structural class, immunostimulatory SNAs (IS-SNAs) efficiently enter endosomes and stimulate immune system signaling via, e.g., toll-like receptor 9 (TLR9), TLR3, and/or TLR7/8). FIG. 3 depicts the use of SNAs as a vaccine for cancer, while FIG. 4 illustrates the use of SNAs for T-cell-based therapy. When used as an enabler for T-cell-based therapy, the initial interaction of the SNAs is with T-cells rather than antigen-presenting cells (APCs). Also, the interaction between SNAs and T-cells takes place ex vivo, and T-cells loaded with SNAs are then re-administered to the subject. The immune response is then generated by the T-cells containing SNAs.

Nanoparticles are therefore provided which are functionalized to have a polynucleotide attached thereto. In general, nanoparticles contemplated include any compound or substance with a high loading capacity for a polynucleotide as described herein, including for example and without limitation, a metal, a semiconductor, a liposomal particle, insulator particle compositions, and a dendrimer (organic versus inorganic).

Thus, nanoparticles are contemplated which comprise a variety of inorganic materials including, but not limited to, metals, semi-conductor materials or ceramics as described in U.S. Patent Publication No 20030147966. For example, metal-based nanoparticles include those described herein. Ceramic nanoparticle materials include, but are not limited to, brushite, tricalcium phosphate, alumina, silica, and zirconia. Organic materials from which nanoparticles are produced include carbon. Nanoparticle polymers include polystyrene, silicone rubber, polycarbonate, polyurethanes, polypropylenes, polymethylmethacrylate, polyvinyl chloride, polyesters, polyethers, and polyethylene. Biodegradable, biopolymer (e.g., polypeptides such as BSA, polysaccharides, etc.), other biological materials (e.g., carbohydrates), and/or polymeric compounds are also contemplated for use in producing nanoparticles.

Liposomal particles, for example as disclosed in International Patent Application No. PCT/US2014/068429 (incorporated by reference herein in its entirety, particularly with respect to the discussion of liposomal particles) are also contemplated by the disclosure. Hollow particles, for example as described in U.S. Patent Publication Number 2012/0282186 (incorporated by reference herein in its entirety) are also contemplated herein. Liposomal particles of the disclosure have at least a substantially spherical geometry, an internal side and an external side, and comprise a lipid bilayer. The lipid bilayer comprises, in various embodiments, a lipid from the phosphocholine family of lipids or the phosphoethanolamine family of lipids. While not meant to be limiting, the first-lipid is chosen from group consisting of 1,2-dioleoyl-sn-glycero-3-phosphocholine (DOPC), 1,2-dimyristoyl-sn-phosphatidylcholine (DMPC), 1-palmitoyl-2-oleoyl-sn-phosphatidylcholine (POPC), 1,2-distearoyl-sn-glycero-3-phospho-(1'-rac-glycerol) (DSPG), 1,2-dioleoyl-sn-glycero-3-phospho-(1'-rac-glycerol) (DOPG), 1,2-distearoyl-sn-glycero-3-phosphocholine (DSPC), 1,2-dipalmitoyl-sn-glycero-3-phosphocholine (DPPC), 1,2-di-(9Z-octadecenoyl)-sn-glycero-3-phosphoethanolamine (DOPE), 1,2-dihexadecanoyl-sn-glycero-3-phosphoethanolamine (DPPE), cardiolipin, lipid A, and a combination thereof.

In one embodiment, the nanoparticle is metallic, and in various aspects, the nanoparticle is a colloidal metal. Thus, in various embodiments, nanoparticles useful in the practice of the methods include metal (including for example and without limitation, gold, silver, platinum, aluminum, palladium, copper, cobalt, indium, nickel, or any other metal amenable to nanoparticle formation), semiconductor (including for example and without limitation, CdSe, CdS, and CdS or CdSe coated with ZnS) and magnetic (for example, ferromagnetite) colloidal materials. Other nanoparticles useful in the practice of the invention include, also without limitation, ZnS, ZnO, Ti, TiO2, Sn, SnO2, Si, SiO2, Fe, Fe+4, Ag, Cu, Ni, Al, steel, cobalt-chrome alloys, Cd, titanium alloys, AgI, AgBr, HgI2, PbS, PbSe, ZnTe, CdTe, In2S3, In2Se3, Cd3P2, Cd3As2, InAs, and GaAs. Methods of making ZnS, ZnO, TiO2, AgI, AgBr, HgI2, PbS, PbSe, ZnTe, CdTe, In2S3, In2Se3, Cd3P2, Cd3As2, InAs, and GaAs nanoparticles are also known in the art. See, e.g., Weller, Angew. Chem. Int. Ed. Engl., 32, 41 (1993); Henglein, Top. Curr. Chem., 143, 113 (1988); Henglein, Chem. Rev., 89, 1861 (1989); Brus, Appl. Phys. A., 53, 465 (1991); Bahncmann, in Photochemical Conversion and Storage of Solar Energy (eds. Pelizetti and Schiavello 1991), page 251; Wang and Herron, J. Phys. Chem., 95, 525 (1991); Olshavsky, et al., J. Am. Chem. Soc., 112, 9438 (1990); Ushida et al., J. Phys. Chem., 95, 5382 (1992).

In practice, methods of increasing cellular uptake and inhibiting gene expression are provided using any suitable particle having oligonucleotides attached thereto that do not interfere with complex formation, i.e., hybridization to a target polynucleotide. The size, shape and chemical composition of the particles contribute to the properties of the resulting oligonucleotide-functionalized nanoparticle. These properties include for example, optical properties, optoelectronic properties, electrochemical properties, electronic properties, stability in various solutions, magnetic properties, and pore and channel size variation. The use of mixtures of particles having different sizes, shapes and/or chemical compositions, as well as the use of nanoparticles having uniform sizes, shapes and chemical composition, is contemplated. Examples of suitable particles include, without limitation, nanoparticles particles, aggregate particles, isotropic (such as spherical particles) and anisotropic particles (such as non-spherical rods, tetrahedral, prisms) and core-shell particles such as the ones described in U.S. patent application Ser. No. 10/034,451, filed Dec. 28, 2002, and International Application No. PCT/US01/50825, filed Dec. 28, 2002, the disclosures of which are incorporated by reference in their entirety.

Methods of making metal, semiconductor and magnetic nanoparticles are well-known in the art. See, for example, Schmid, G. (ed.) Clusters and Colloids (VCH, Weinheim, 1994); Hayat, M. A. (ed.) Colloidal Gold: Principles, Methods, and Applications (Academic Press, San Diego, 1991); Massart, R., IEEE Transactions On Magnetics, 17, 1247 (1981); Ahmadi, T. S. et al., Science, 272, 1924 (1996); Henglein, A. et al., J. Phys. Chem., 99, 14129 (1995); Curtis, A. C., et al., Angew. Chem. Int. Ed. Engl., 27, 1530 (1988). Preparation of polyalkylcyanoacrylate nanoparticles prepared is described in Fattal, et al., J. Controlled Release (1998) 53: 137-143 and U.S. Pat. No. 4,489,055. Methods for making nanoparticles comprising poly(D-glucaramido-amine)s are described in Liu, et al., J. Am. Chem. Soc. (2004) 126:7422-7423. Preparation of nanoparticles comprising polymerized methylmethacrylate (MMA) is described in Tondelli, et al., Nucl. Acids Res. (1998) 26:5425-5431, and preparation of dendrimer nanoparticles is described in, for example Kukowska-Latallo, et al., Proc. Natl. Acad. Sci. USA (1996) 93:4897-4902 (Starburst polyamidoamine dendrimers)

Suitable nanoparticles are also commercially available from, for example, Ted Pella, Inc. (gold), Amersham Corporation (gold) and Nanoprobes, Inc. (gold).

Also as described in US Patent Publication No. 20030147966, nanoparticles comprising materials described herein are available commercially or they can be produced from progressive nucleation in solution (e.g., by colloid reaction), or by various physical and chemical vapor deposition processes, such as sputter deposition. See, e.g., HaVashi, (1987) Vac. Sci. Technol. July/August 1987, A5(4):1375-84; Hayashi, (1987) Physics Today, December 1987, pp. 44-60; MRS Bulletin, January 1990, pgs. 16-47.

As further described in U.S. Patent Publication No. 20030147966, nanoparticles contemplated are produced using $HAuCl_4$ and a citrate-reducing agent, using methods known in the art. See, e.g., Marinakos et al., (1999) Adv. Mater. 11: 34-37; Marinakos et al., (1998) Chem. Mater. 10: 1214-19; Enustun & Turkevich, (1963) J. Am. Chem. Soc. 85: 3317. Tin oxide nanoparticles having a dispersed aggregate particle size of about 140 nm are available commercially from Vacuum Metallurgical Co., Ltd. of Chiba, Japan. Other commercially available nanoparticles of various compositions and size ranges are available, for example, from Vector Laboratories, Inc. of Burlingame, Calif.

Nanoparticles can range in size from about 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 nm in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, about 1 nm to about 10 nm in mean diameter. In other aspects, the size of the nanoparticles is from about 5 nm to about 150 nm (mean diameter), from about 5 to about 50 nm, from about 10 to about 30 nm, from about 10 to 150 nm, from about 10 to about 100 nm, or about 10 to about 50 nm. The size of the nanoparticles is from about 5 nm to about 150 nm (mean diameter), from about 30 to about 100 nm, from about 40 to about 80 nm. The size of the nanoparticles used in a method varies as required by their particular use or application. The variation of size is advantageously used to optimize certain physical characteristics of the nanoparticles, for example, optical properties or the amount of surface area that can be functionalized as described herein. In further embodiments, a plurality of SNAs (e.g., liposomal particles) is produced and the SNAs in the plurality have a mean diameter of less than or equal to about 50 nanometers (e.g., about 5 nanometers to about 50 nanometers, or about 5 nanometers to about 40 nanometers, or about 5 nanometers to about 30 nanometers, or about 5 nanometers to about 20 nanometers, or about 10 nanometers to about 50 nanometers, or about 10 nanometers to about 40 nanometers, or about 10 nanometers to about 30 nanometers, or about 10 nanometers to about 20 nanometers). In further embodiments, the SNAs in the plurality created by a method of the disclosure have a mean diameter of less than or equal to about 20 nanometers, or less than or equal to about 25 nanometers, or less than or equal to about 30 nanometers, or less than or equal to about 35 nanometers, or less than or equal to about 40 nanometers, or less than or equal to about 45 nanometers.

Antigen.

The present disclosure provides SNAs comprising an antigen. In various embodiments, the antigen is a tumor-associated antigen. In some embodiments, the antigen is a prostate-specific antigen (PSA) peptide, mesothelin, glycoprotein 100 (gp100), prostate specific membrane antigen (PSMA), or prostatic acid phosphatase (PAP). Other antigens are contemplated for use according to the compositions and methods of the disclosure; any antigen for which an immune response is desired is contemplated herein.

It is contemplated herein that an antigen for use in the compositions and methods of the disclosure are encapsulated with a SNA, or an antigen is on the surface of the SNA, or both.

Cells.

The disclosure contemplates contacting a SNA as described herein with a cell in order to load the cell with an immunostimulatory oligonucleotide and a tumor-associated antigen. Cells contemplated for use in the compositions and methods of the disclosure include, but are not limited to, a T-cell, a natural killer (NK) cell, a B-cell, a macrophage, a dendritic cell, or a combination thereof.

Polynucleotides.

The term "nucleotide" or its plural as used herein is interchangeable with modified forms as discussed herein and otherwise known in the art. In certain instances, the art uses the term "nucleobase" which embraces naturally-occurring nucleotide, and non-naturally-occurring nucleotides which include modified nucleotides. Thus, nucleotide or nucleobase means the naturally occurring nucleobases A, G, C, T, and U. Non-naturally occurring nucleobases include, for example and without limitations, xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-(C3-C6)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, polynucleotides also include one or more "nucleosidic bases" or "base units" which are a category of non-naturally-occurring nucleotides that include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Modified nucleotides are described in EP 1 072 679 and WO 97/12896, the disclosures of which are incorporated herein by reference. Modified nucleobases include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

Nanoparticles provided that are functionalized with a polynucleotide, or a modified form thereof generally comprise a polynucleotide from about 5 nucleotides to about 100 nucleotides in length. More specifically, nanoparticles are functionalized with a polynucleotide that is about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all polynucleotides intermediate in length of the sizes specifically disclosed to the extent that the polynucleotide is able to achieve the desired result. Accordingly, polynucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 125, about 150, about 175, about 200, about 250, about 300, about 350, about 400, about 450, about 500 or more nucleotides in length are contemplated.

In some embodiments, the polynucleotide attached to a nanoparticle is DNA. When DNA is attached to the nanoparticle, the DNA is in some embodiments comprised of a sequence that is sufficiently complementary to a target region of a polynucleotide such that hybridization of the DNA polynucleotide attached to a nanoparticle and the target polynucleotide takes place, thereby associating the target polynucleotide to the nanoparticle. The DNA in various aspects is single stranded or double-stranded, as long as the double-stranded molecule also includes a single strand region that hybridizes to a single strand region of the target polynucleotide. In some aspects, hybridization of the polynucleotide functionalized on the nanoparticle can form a triplex structure with a double-stranded target polynucleotide. In another aspect, a triplex structure can be formed by hybridization of a double-stranded oligonucleotide functionalized on a nanoparticle to a single-stranded target polynucleotide.

In some embodiments, the disclosure contemplates that a polynucleotide attached to a nanoparticle is RNA. The RNA can be either single-stranded or double-stranded, so long as it is able to hybridize to a target polynucleotide.

In some aspects, multiple polynucleotides are functionalized to a nanoparticle. In various aspects, the multiple polynucleotides each have the same sequence, while in other aspects one or more polynucleotides have a different sequence. In further aspects, multiple polynucleotides are arranged in tandem and are separated by a spacer. Spacers are described in more detail herein below.

Polynucleotide Attachment to a Nanoparticle.

Polynucleotides contemplated for use in the methods include those bound to the nanoparticle through any means (e.g., covalent or non-covalent attachment). Regardless of the means by which the polynucleotide is attached to the nanoparticle, attachment in various aspects is effected through a 5' linkage, a 3' linkage, some type of internal linkage, or any combination of these attachments. In some embodiments, the polynucleotide is covalently attached to a nanoparticle. In further embodiments, the polynucleotide is non-covalently attached to a nanoparticle. An oligonucleotide of the disclosure comprises, in various embodiments, a tocopherol, a cholesterol moiety, DOPE-butamide-phenyl-maleimido, or lyso-phosphoethanolamine-butamide-pneyl-maleimido. See also U.S. Patent Application Publication No. 2016/0310425, incorporated by reference herein in its entirety.

Methods of attachment are known to those of ordinary skill in the art and are described in US Publication No. 2009/0209629, which is incorporated by reference herein in its entirety. Methods of attaching RNA to a nanoparticle are generally described in PCT/US2009/65822, which is incorporated by reference herein in its entirety. Methods of associating polynucleotides with a liposomal particle are described in PCT/US2014/068429, which is incorporated by reference herein in its entirety.

Spacers.

In certain aspects, functionalized nanoparticles are contemplated which include those wherein an oligonucleotide is attached to the nanoparticle through a spacer. "Spacer" as used herein means a moiety that does not participate in modulating gene expression per se but which serves to increase distance between the nanoparticle and the functional oligonucleotide, or to increase distance between individual oligonucleotides when attached to the nanoparticle in multiple copies. Thus, spacers are contemplated being located between individual oligonucleotides in tandem, whether the oligonucleotides have the same sequence or have different sequences. In some aspects, the spacer when present is an organic moiety. In another aspect, the spacer is a polymer, including but not limited to a water-soluble polymer, a polynucleotide, a polypeptide, an oligosaccharide, a carbohydrate, a lipid, an ethylglycol, or combinations thereof.

In certain aspects, the polynucleotide has a spacer through which it is covalently bound to the nanoparticles. As a result of the binding of the spacer to the nanoparticles, the polynucleotide is spaced away from the surface of the nanoparticles and is more accessible for hybridization with its target. In various embodiments, the length of the spacer is or is equivalent to at least about 5 nucleotides, 5-10 nucleotides, 10 nucleotides, 10-30 nucleotides, or even greater than 30 nucleotides. The spacer may have any sequence which does not interfere with the ability of the polynucleotides to become bound to the nanoparticles or to the target polynucleotide. In certain aspects, the bases of a polynucleotide spacer are all adenylic acids, all thymidylic acids, all cytidylic acids, all guanylic acids, all uridylic acids, or all some other modified base.

Nanoparticle Surface Density.

A surface density adequate to make the nanoparticles stable and the conditions necessary to obtain it for a desired combination of nanoparticles and polynucleotides can be determined empirically. Generally, a surface density of at least about 2 pmoles/cm$^2$ will be adequate to provide stable nanoparticle-oligonucleotide compositions. In some aspects, the surface density is at least 15 pmoles/cm$^2$. Methods are also provided wherein the polynucleotide is bound to the nanoparticle at a surface density of at least 2 pmol/cm$^2$, at least 3 pmol/cm$^2$, at least 4 pmol/cm$^2$, at least 5 pmol/cm$^2$, at least 6 pmol/cm$^2$, at least 7 pmol/cm$^2$, at least 8 pmol/cm$^2$, at least 9 pmol/cm$^2$, at least 10 pmol/cm$^2$, at least about 15 pmol/cm2, at least about 19 pmol/cm$^2$, at least about 20 pmol/cm$^2$, at least about 25 pmol/cm$^2$, at least about 30 pmol/cm$^2$, at least about 35 pmol/cm$^2$, at least about 40 pmol/cm$^2$, at least about 45 pmol/cm$^2$, at least about 50 pmol/cm$^2$, at least about 55 pmol/cm$^2$, at least about 60 pmol/cm$^2$, at least about 65 pmol/cm$^2$, at least about 70 pmol/cm$^2$, at least about 75 pmol/cm$^2$, at least about 80 pmol/cm$^2$, at least about 85 pmol/cm$^2$, at least about 90 pmol/cm$^2$, at least about 95 pmol/cm$^2$, at least about 100 pmol/cm$^2$, at least about 125 pmol/cm$^2$, at least about 150 pmol/cm$^2$, at least about 175 pmol/cm$^2$, at least about 200 pmol/cm$^2$, at least about 250 pmol/cm$^2$, at least about 300 pmol/cm$^2$, at least about 350 pmol/cm$^2$, at least about 400 pmol/cm$^2$, at least about 450 pmol/cm$^2$, at least about 500 pmol/cm$^2$, at least about 550 pmol/cm$^2$, at least about 600 pmol/cm$^2$, at least about 650 pmol/cm$^2$, at least about 700 pmol/cm$^2$, at least about 750 pmol/cm$^2$, at least about 800 pmol/cm$^2$, at least about 850 pmol/cm$^2$, at least about 900 pmol/cm$^2$, at least about 950 pmol/cm$^2$, at least about 1000 pmol/cm$^2$ or more.

Alternatively, the density of polynucleotide on the surface of the SNA is measured by the number of polynucleotides on the surface of a SNA. With respect to the surface density of polynucleotides on the surface of a SNA of the disclosure, it is contemplated that a SNA as described herein comprises from about 1 to about 100 oligonucleotides on its surface. In various embodiments, a SNA comprises from about 10 to about 100, or from 10 to about 90, or from about 10 to about 80, or from about 10 to about 70, or from about 10 to about 60, or from about 10 to about 50, or from about 10 to about 40, or from about 10 to about 30, or from about 10 to about 20 oligonucleotides on its surface. In further embodiments, a SNA comprises at least about 5, 10, 20, 30, 40, 45, 50, 55, 60, 65, 70, 75, 80, 85, 90, 95, or 100 polynucleotides on its surface.

Uses of SNAs in Gene Regulation/Therapy

In addition to serving a role in providing an oligonucleotide (e.g., an immunostimulatory oligonucleotide) and a tumor-associated antigen to a cell, it is also contemplated that in some embodiments, a SNA of the disclosure possesses the ability to regulate gene expression. In other words, in some aspects the disclosure provides a SNA comprising an oligonucleotide (e.g., an immunostimulatory oligonucleotide), a tumor-associated antigen, and an additional oligonucleotide designed to effect inhibition of target gene expression or perform some other regulatory function (e.g., target cell recognition). Accordingly, in some embodiments the disclosure provides methods for inhibiting gene product expression, and such methods include those wherein expression of a target gene product is inhibited by about or at least about 5%, about or at least about 10%, about or at least about 15%, about or at least about 20%, about or at least about 25%, about or at least about 30%, about or at least about 35%, about or at least about 40%, about or at least about 45%, about or at least about 50%, about or at least about 55%, about or at least about 60%, about or at least about 65%, about or at least about 70%, about or at least about 75%, about or at least about 80%, about or at least about 85%, about or at least about 90%, about or at least about 95%, about or at least about 96%, about or at least about 97%, about or at least about 98%, about or at least about 99%, or 100% compared to gene product expression in the absence of a SNA. In other words, methods provided embrace those which results in essentially any degree of inhibition of expression of a target gene product.

The degree of inhibition is determined in vivo from a body fluid sample or from a biopsy sample or by imaging techniques well known in the art. Alternatively, the degree of inhibition is determined in a cell culture assay, generally as a predictable measure of a degree of inhibition that can be expected in vivo resulting from use of a specific type of SNA and a specific oligonucleotide.

In various aspects, the methods include use of an oligonucleotide which is 100% complementary to the target polynucleotide, i.e., a perfect match, while in other aspects, the oligonucleotide is at least (meaning greater than or equal to) about 95% complementary to the polynucleotide over the length of the oligonucleotide, about or at least about 90%, about or at least about 85%, about or at least about 80%, about or at least about 75%, about or at least about 70%, about or at least about 65%, about or at least about 60%, about or at least about 55%, about or at least about 50%, about or at least about 45%, about or at least about 40%, about or at least about 35%, about or at least about 30%, about or at least about 25%, about or at least about 20% complementary to the polynucleotide over the length of the oligonucleotide to the extent that the oligonucleotide is able to achieve the desired degree of inhibition of a target gene product. Moreover, an oligonucleotide may hybridize over one or more segments such that intervening or adjacent segments are not involved in the hybridization event (e.g., a loop structure or hairpin structure). The percent complementarity is determined over the length of the oligonucleotide. For example, given an inhibitory oligonucleotide in which 18 of 20 nucleotides of the inhibitory oligonucleotide are complementary to a 20 nucleotide region in a target polynucleotide of 100 nucleotides total length, the oligonucleotide would be 90 percent complementary. In this example, the remaining noncomplementary nucleotides may be clustered or interspersed with complementary nucleobases and need not be contiguous to each other or to complementary nucleotides. Percent complementarity of an inhibitory oligonucleotide with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Accordingly, methods of utilizing a SNA of the disclosure in gene regulation therapy are provided. This method comprises the step of hybridizing a polynucleotide encoding the gene with one or more oligonucleotides complementary to all or a portion of the polynucleotide, the oligonucleotide being the additional oligonucleotide of a composition as described herein, wherein hybridizing between the polynucleotide and the oligonucleotide occurs over a length of the polynucleotide with a degree of complementarity sufficient to inhibit expression of the gene product. The inhibition of gene expression may occur in vivo or in vitro.

The oligonucleotide utilized in the methods of the disclosure is either RNA or DNA. The RNA can be an inhibitory RNA (RNAi) that performs a regulatory function, and in various embodiments is selected from the group consisting of a small inhibitory RNA (siRNA), an RNA that forms a triplex with double stranded DNA, and a ribozyme. Alternatively, the RNA is microRNA that performs a regulatory function. The DNA is, in some embodiments, an antisense-DNA.

In various embodiments, the target polynucleotide encodes programmed death 1 (PD-1) or programmed death-ligand 1 (PD-L1).

Use of SNAs in Immune Regulation

Toll-like receptors (TLRs) are a class of proteins, expressed in sentinel cells, that plays a key role in regulation of innate immune system. The mammalian immune system uses two general strategies to combat infectious diseases. Pathogen exposure rapidly triggers an innate immune response that is characterized by the production of immunostimulatory cytokines, chemokines and polyreactive IgM antibodies. The innate immune system is activated by exposure to Pathogen Associated Molecular Patterns (PAMPs) that are expressed by a diverse group of infectious microorganisms. The recognition of PAMPs is mediated by members of the Toll-like family of receptors. TLR receptors, such as TLR 4, TLR 8 and TLR 9 that respond to specific oligonucleotide are located inside special intracellular compartments, called endosomes. The mechanism of modulation of TLR 4, TLR 8 and TLR9 receptors is based on DNA-protein interactions.

Synthetic immunostimulatory oligonucleotides that contain CpG motifs that are similar to those found in bacterial DNA stimulate a similar response of the TLR receptors. Therefore immunomodulatory oligonucleotides have various potential therapeutic uses, including treatment of immune deficiency and cancer.

Down regulation of the immune system would involve knocking down the gene responsible for the expression of the Toll-like receptor. This antisense approach involves use of SNAs conjugated to specific antisense oligonucleotide sequences to knock down the expression of any toll-like protein.

Accordingly, methods of utilizing SNAs for modulating toll-like receptors are disclosed. The method either up-regulates or down-regulates the Toll-like-receptor through the use of a TLR agonist or a TLR antagonist, respectively. The method comprises contacting a cell having a toll-like receptor with a SNA of the disclosure. The toll-like receptors modulated include toll-like receptor 1, toll-like receptor 2, toll-like receptor 3, toll-like receptor 4, toll-like receptor 5, toll-like receptor 6, toll-like receptor 7, toll-like receptor 8, toll-like receptor 9, toll-like receptor 10, toll-like receptor 11, toll-like receptor 12, and toll-like receptor 13.

Compositions.

The disclosure includes compositions that comprise a pharmaceutically acceptable carrier and a cell having a spherical nucleic acid (SNA) contained therein, wherein the cell is obtained from an individual and the SNA comprises a nanoparticle, an oligonucleotide on the surface of the nanoparticle, and an antigen. In some embodiments, the composition is an antigenic composition. The term "carrier" refers to a vehicle within which the SNA is administered to a mammalian subject. The term carrier encompasses diluents, excipients, adjuvants and combinations thereof. Pharmaceutically acceptable carriers are well known in the art (see, e.g., Remington's Pharmaceutical Sciences by Martin, 1975).

Exemplary "diluents" include sterile liquids such as sterile water, saline solutions, and buffers (e.g., phosphate, tris, borate, succinate, or histidine). Exemplary "excipients" are inert substances include but are not limited to polymers (e.g., polyethylene glycol), carbohydrates (e.g., starch, glucose, lactose, sucrose, or cellulose), and alcohols (e.g., glycerol, sorbitol, or xylitol).

Adjuvants are include but are not limited to emulsions, microparticles, immune stimulating complexes (iscoms), LPS, CpG, or MPL.

Adoptive Cell Therapy.

The disclosure includes methods of treating an individual in need of adoptive cell therapy, comprising administering to the individual an effective amount of a composition of the disclosure. Adoptive cell therapy involves isolating cells from an individual, expanding the cells ex vivo, and infusing the cells back to the patient.

For adoptive cell therapy using antigen-specific cells, cell doses in the range of about $10^6$ to about $10^{10}$ (e.g., about $10^9$) are typically infused. Upon administration of the cells into the subject and subsequent differentiation, the cells are induced that are specifically directed against one specific antigen (e.g., a tumor-associated antigen). The cells of the presently disclosed subject matter can be administered by any methods known in the art, including, but not limited to, pleural administration, intravenous administration, subcutaneous administration, intranodal administration, intratumoral administration, intrathecal administration, intrapleural administration, intraperitoneal administration, and direct administration to the thymus. In certain embodiments, the cells are intravenously administered to the subject in need.

The presently disclosed subject matter provides various methods of using the cells (e.g., T cells) expressing a tumor-associate antigen. For example, the presently disclosed subject matter provides methods of reducing tumor burden in a subject. In one non-limiting example, the method of reducing tumor burden comprises administering an effective amount of the presently disclosed composition to the subject, thereby inducing tumor cell death in the subject. The presently disclosed cell can reduce the number of tumor cells, reduce tumor size, and/or eradicate the tumor in the subject. Non-limiting examples of an individual in need of a composition of the disclosure include those individuals suffering from a cancer selected from the group consisting of prostate, breast, melanoma, and lung cancer.

The presently disclosed subject matter also provides methods of increasing or lengthening survival of a subject having cancer. In some embodiments, the method of increasing or lengthening survival of a subject having cancer comprises administering an effective amount of a composition of the disclosure to the subject, thereby increasing or lengthening survival of the subject. The method can reduce or eradicate tumor burden in the subject.

Methods of Inducing an Immune Response.

The disclosure includes methods for eliciting an immune response in a subject in need thereof, comprising administering to the subject an effective amount of a composition or vaccine of the disclosure.

The immune response raised by the methods of the present disclosure generally includes an antibody response, preferably a neutralizing antibody response, preferably a protective antibody response. The immune response generated by a composition as disclosed herein is directed against, and preferably ameliorates and/or neutralizes and/or reduces the tumor burden of cancer. Methods for assessing antibody responses after administration of a composition of the disclosure (immunization or vaccination) are known in the art and/or described herein. In some embodiments, the immune response comprises a T cell-mediated response (e.g., peptide-specific response such as a proliferative response or a cytokine response). In preferred embodiments, the immune response comprises both a B cell and a T cell response. Antigenic compositions can be administered in a number of suitable ways, such as intramuscular injection, subcutaneous injection, intradermal administration and mucosal administration such as oral or intranasal. Additional modes of administration include but are not limited to intranasal administration, and oral administration.

Antigenic compositions may be used to treat both children and adults. Thus a subject may be less than 1 year old, 1-5 years old, 5-15 years old, 15-55 years old, or at least 55 years old. Preferred subjects for receiving the vaccines are the elderly (e.g., >55 years old, >60 years old, preferably >65 years old), and the young (e.g., <6 years old, 1-5 years old, preferably less than 1 year old).

Administration can involve a single dose or a multiple dose schedule. Multiple doses may be used in a primary immunization schedule and/or in a booster immunization schedule. In a multiple dose schedule the various doses may be given by the same or different routes, e.g., a parenteral prime and mucosal boost, or a mucosal prime and parenteral boost. Administration of more than one dose (typically two doses) is particularly useful in immunologically naïve subjects or subjects of a hyporesponsive population (e.g., diabetics, or subjects with chronic kidney disease). Multiple doses will typically be administered at least 1 week apart (e.g., about 2 weeks, about 3 weeks, about 4 weeks, about 6 weeks, about 8 weeks, about 10 weeks, about 12 weeks, or about 16 weeks). Preferably multiple doses are administered from one, two, three, four or five months apart. Antigenic compositions of the present disclosure may be administered to patients at substantially the same time as (e.g., during the same medical consultation or visit to a healthcare professional) other vaccines.

In general, the number of cells (comprising SNAs as disclosed herein) in each dose of the antigenic composition is selected as an amount effective to induce an immune response in the subject, without causing significant, adverse side effects in the subject. Preferably the immune response elicited is a neutralizing antibody, preferably a protective antibody response. The number of cells to be administered is, in various embodiments, about 100,000 to $1\times10^6$, or about 500,000 to about $1\times10^6$, or about $1\times10^6$ to about $5\times10^6$, or about $1\times10^6$ to about $1\times10^{10}$.

Articles of Manufacture and Kits.

The disclosure additionally includes articles of manufacture and kits comprising a composition described herein. In some embodiments, the kits further comprise instructions for measuring antigen-specific antibodies. In some embodiments, the antibodies are present in serum from a blood sample of a subject immunized with a composition comprising an SNA of the disclosure.

As used herein, the term "instructions" refers to directions for using reagents contained in the kit for measuring antibody titer. In some embodiments, the instructions further comprise the statement of intended use required by the U.S. Food and Drug Administration (FDA) in labeling in vitro diagnostic products.

The following examples illustrate various embodiments contemplated by the present disclosure. The figures provided herein are exemplary in nature and are in no way intended to be limiting.

EXAMPLES

Example 1

Materials and Methods

Mice and Reagents.

C57BL/6 WT, and Pmel-1 mice were purchased from Jackson Laboratory. OT-1 Rag1−/− mice were purchased from Taconic. Dr. Hans Schreiber (University of Chicago) provided B16F10 cell line. All the cell lines were routinely tested for *mycoplasma* infections by culture and DNA stain, and maintained in complete medium composed of RPMI 1640 with 10% FBS. All animal experiments were approved by institutional animal use committees of Northwestern University. All mAbs were obtained from eBiosciences and BioLegend. Proliferation dye eFluor 450 was from eBiosciences.

SNAs, Oligonucleotides, and Antigens.

For SNA and admix controls the peptides hgp10025-33 and OVA257-264 were purchased from Anaspec. Oligonucleotides were synthesized using automated solid support phosphoramidite synthesis. SNAs were synthesized as described [Banga et al., Journal of the American Chemical Society. 2014; 136(28):9866-9]. SNAs consisted of cholesterol-terminated CpG oligonucleotides (3'-TC-CATGACGTTCCTGACGTT-5' (SEQ ID NO: 1)) with phosphorthioate internucleotide linkages, adsorbed onto 50-nm diameter DOPC (di-oleoylphosphocholine) liposomes prepared by membrane extrusion. Peptide antigens were incorporated into SNA structures by encapsulation within liposomes. SNAs were purified from unadsorbed oligonucleotide and from unincorporated antigen by tangential flow filtration, or filtration through polycarbonate filters and resuspension in PBS.

Analysis of Cells by Flow Cytometry.

All samples were initially incubated with 2.4G2 to block antibody binding to Fc receptors. Single-cell suspensions were stained with 1 µg of relevant mAbs and then washed twice with cold PBS. Cytokine detection was performed by restimulating $1-3\times10^6$ cells in single cell suspensions in a cocktail of 17 µg/mL of Brefeldin A, 50 ng/mL of PMA, and 1 µg/mL of ionomycin for 4 hours in RPMI 1640 supplemented with 10% FBS prior to following manufacturer protocol for intracellular cytokine staining (BD Biosciences).

In Vivo Tumor Challenges and T Chaperone Therapy.

B16F10 or LLC1-OVA ($1\times10^6$) in suspension were injected s.c. into the rear right flank of mice. On day 8 or when tumors reached approximately 150 mm³, T chaperones were transferred i.v. in a volume of 200 µl of PBS. Prior to infusion, T chaps were generated from naïve T-cells by incubated with controls (mixtures of antigen and oligonucleotide) or SNAs overnight, washed three times and immediately transferred. In all experiments the size of tumor was determined at 2-3 day intervals. Tumor volumes were measured along orthogonal axes (a, b, and c) and calculated as abc/2.

In Vitro Activation of T Chaperones.

In all experiments CD8$^+$ PMEL T cells were selected using EasySep™ CD8$^+$ T cell positive selection kit II from STEMCELL technologies. For overnight activation, 0.5× 10$^6$ T cells were plated in 200 µl of RPMI 1640 supplemented with 10% FBS. gp100 peptide was added at a final concentration of 4 µg/ml and ova-I at 0.06 µg/ml as either free peptide or encapsulated in the core of SNAs. CpG stimulating oligonucleotide or GpC control oligonucleotide was given at 1 µM final concentration as either free linear form or in SNA form. In all experiments cells were washed with PBS three times prior to re-plating or transfer into animal.

Statistical Analysis.

Mean values were compared using an unpaired Student's two-tailed t test. Probability values >0.05 were considered non-significant.

Results

Figure 5:
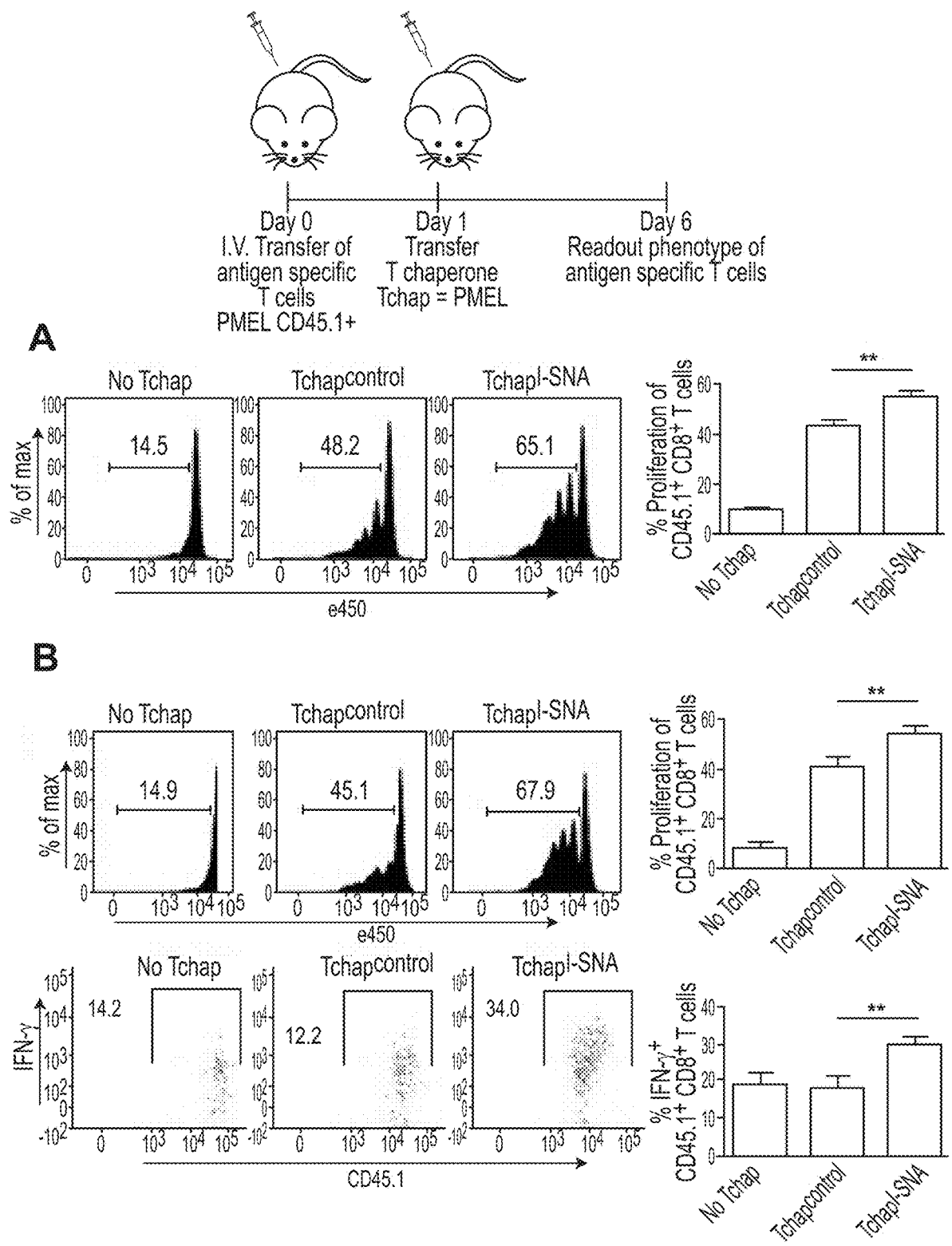
FIG. 5 shows that T chaperones are capable of priming antigen specific CD8+ T cells in vivo. A) Spleen B) Lymph Node. On day zero $3 \times 10^6$ naïve CD45.1$^+$ PMEL T cells were stained with e450 cell proliferation dye and then transferred i.v. into WT C57BL/6 mice. The next day $5 \times 10^6$ T chaperones were transferred i.v. after incubation with either admix CpG/gp100 controls or SNAs overnight at 4 μg/mL of gp100 and 1 μM CpG. On day 6 CD45.1$^+$ T cells were isolated from spleen and inguinal lymph nodes and analyzed for proliferation and IFN-γ production by flow cytometry.

T chaperones (T chaps) possess ability to induce T cell priming in vivo. One goal of immunotherapy is to activate endogenous antigen specific CD8$^+$ T cells to kill cancer cells. The approach disclosed herein is the treatment of T-cells ex vivo with SNAs, to load T-cells with immunestimulatory oligonucleotide and tumor-associated antigen, and to use these cells, "T chaperones" (T chaps), to activate endogenous antigen specific CD8$^+$ T cells. Previous data showed that T chaps can activate naïve CD8$^+$ T cells in vitro, so experiments disclosed herein were designed to demonstrate these effects in vivo. Using an in vivo priming assay, it was found that both T cell chaperones generated by treating naïve T-cells with free CpG and free peptide admix (T chapcontrol) and those generated by treatment with IS-NAs (T chap$_{ISNA}$) were able to induce proliferation of naïve responder cells in both spleen and lymph nodes (FIGS. 5 A,B). However, only T chap$_{ISNA}$ were able to induce the anti-tumor molecule IFN-γ production from naïve PMEL responder T cells in the lymph nodes (FIG. 5A). This correlates well with anti-tumor data and increased IFN-γ production by tumor infiltrating T cells in T chap$_{ISNA}$ treated mice.

T Chap$_{ISNA}$ Retain Long Term Killing Functions.

Figure 6:
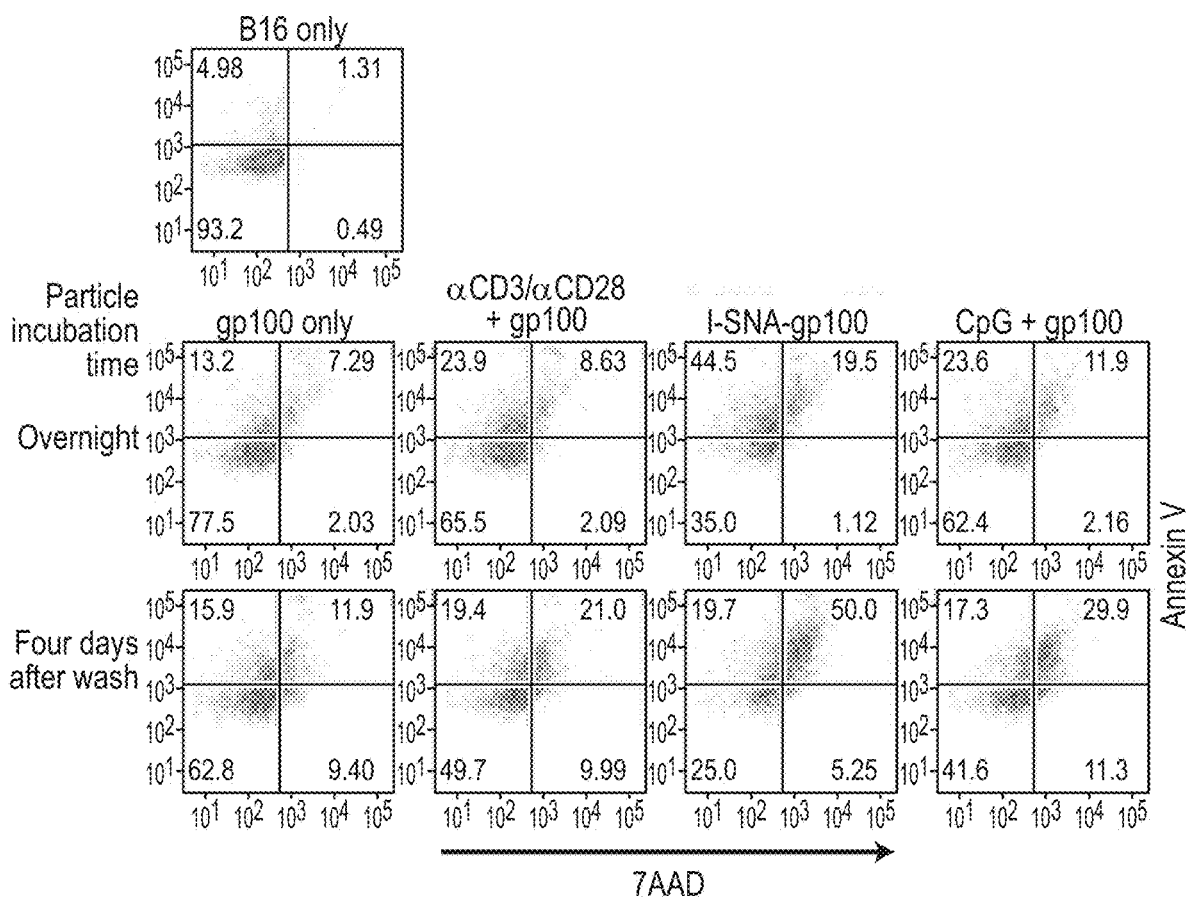
FIG. 6 demonstrates that SNA derived T chaperones promote durable killing function and tumor protection. A) In vitro killing by T chap$_{ISNA}$. Purified CD8$^+$ PMEL T cells were incubated with the labeled conditions overnight, washed and allowed to rest for four days. Overnight controls were incubated one day prior to the assay being performed and plated with B16 cells on the same day as the four day rest group. Before incubation, tumor cells were labeled with e450 dye and gated as CD45− e450$^+$ for analysis of apoptotic markers by flow cytometry. For activation of T cells prior to killing assay αCD3/αCD28 was given at 1 μg/mL, gp100 was given at 4 μg/ml, CpG was at 1 μM. Experiment was plated at a 50:1 ratio of T cell: tumor cell for 12 hours. B) T chap$_{ISNA}$ control B16 tumor growth. C57BL/6 were challenged subcutaneously with $1 \times 10^6$ B16-F10 tumor cells on the hind flank. On day 8, when tumors were approximately 150 mm$^3$, mice were intravenously administered 200 μL of PBS or $10^6$ T chaps in 200 μL of PBS.
Figure 6:
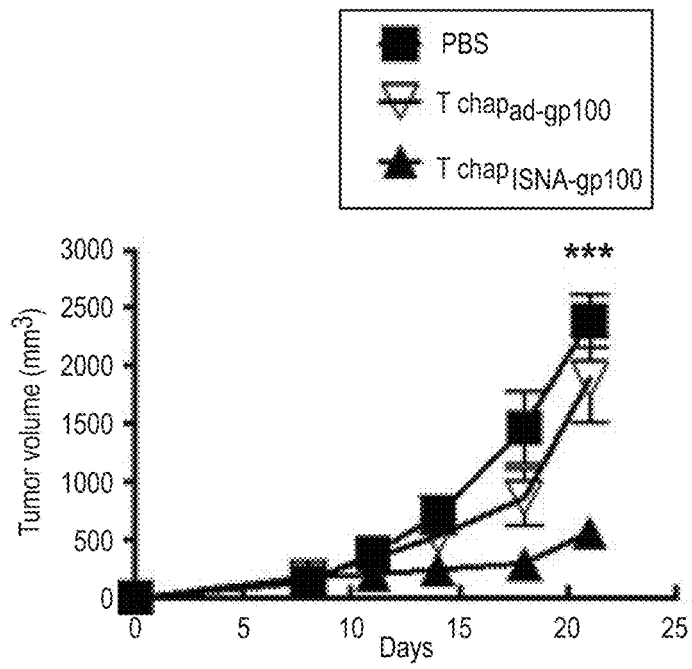

The long term effects of SNAs on T cell effector functions was then tested. A control group consisting of T chaps generated by an overnight stimulation by a variety of immunestimulatory treatments (shown in FIG. 6A was used for comparison with T chaps that were evaluated 4 days following their generation with the same immunestimulatory conditions. The four day experimental group was generated by incubating CD8$^+$ PMEL T cells overnight, washing them the following day and then re-plating in fresh medium in the absence of additional SNAs or control materials for four days. The control group was prepared one day in advance of evaluation by plating with B16 target tumor cells. The results showed that T chap$_{ISNA}$ have better killing function compared to all controls and also have a durable effector response. This suggests a long term programming for killing function initiated by SNAs (FIG. 6A).

Figure 7:
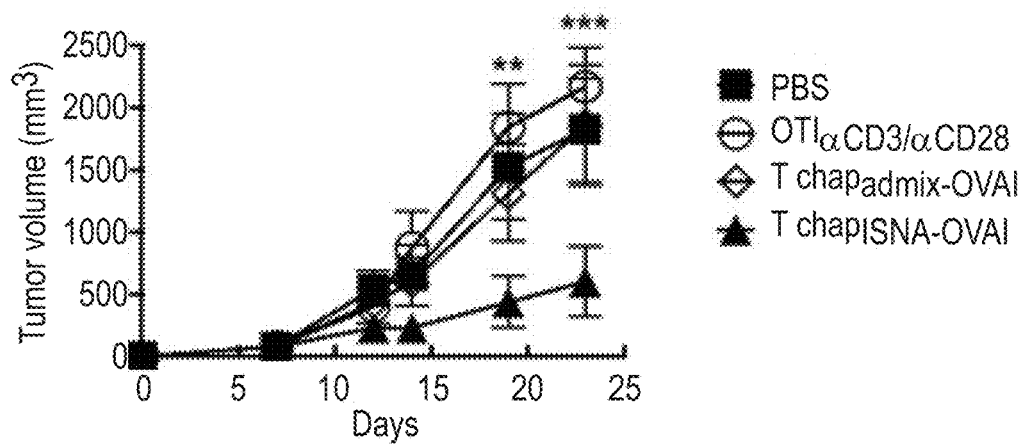
FIG. 7 shows that SNA T chaperones control LLC1-OVA tumors and increase polyfunctional CD8+ T cell tumor infiltrates. A) C57BL/6 were challenged subcutaneously with $1 \times 10^6$ LLC1-OVA tumor cells on the hind flank. On day 8, when tumors were approximately 150 mm$^3$, mice were intravenously administered 200 μL of PBS or $1 \times 10^6$ T chaperones in 200 μL of PBS. T chaperones were prepared by incubating $0.5 \times 10^6$ OT-1 CD8$^+$ T cells in 200 μL volume overnight with 0.06 μg/mL of OVA-I peptide and 1 μM of CpG. Cells were washed three times before transfer B) T chaperones promote tumor infiltration of polyfunctional T cells. When control tumors reached growth limit, on day 23, tumor tissue was analyzed for CD8$^+$ T cell infiltrates by flow cytometry for cytokine production.
Figure 7:
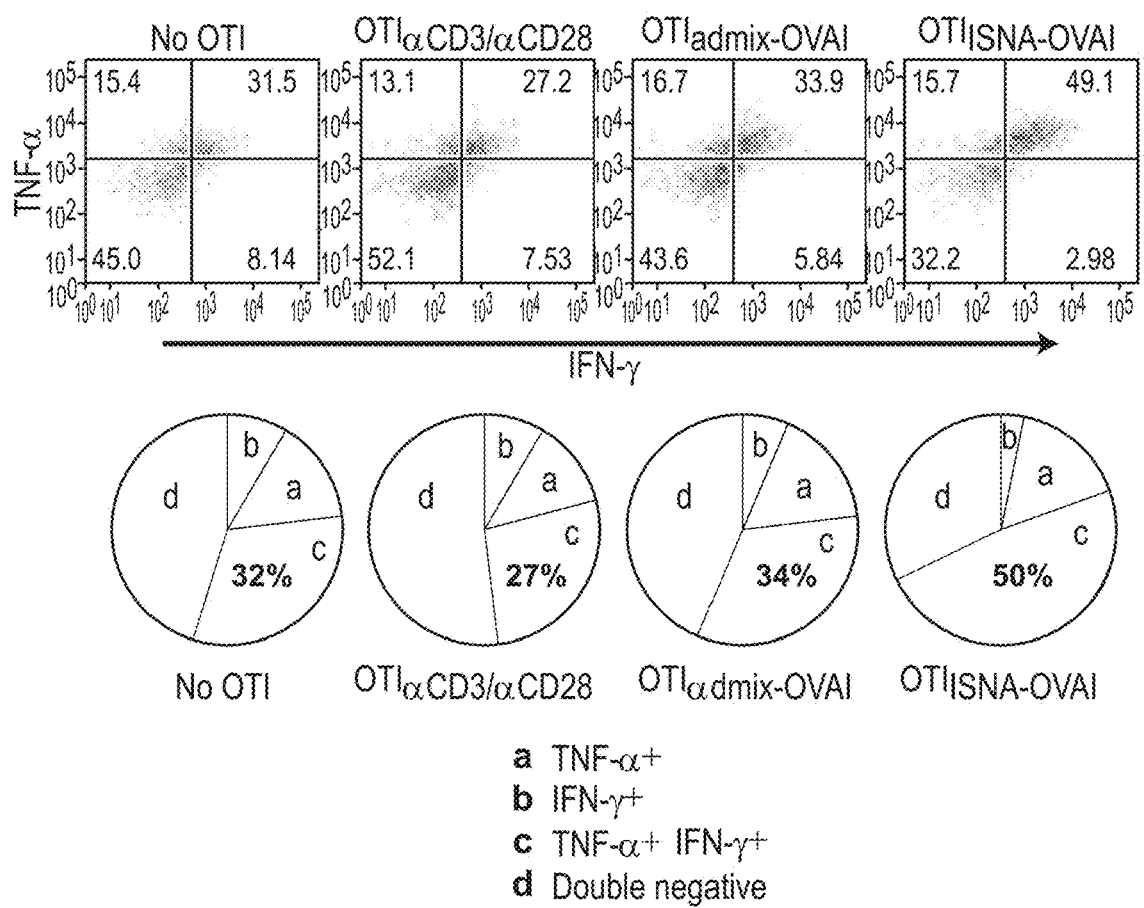

These effects were also seen in in vivo tumor challenges, in the comparison of admix of CpG and antigen and IS-SNAs in the generation of T chaps for adoptive cellular therapy. Using two models, B16 melanoma and LLC1-OVA lung carcinoma (FIG. 6B, 7A) it was observed that T chap$_{ISNA}$ are superior to conventional activation and to admix activation to control both models. In the tumor microenvironment it was found that T chap$_{ISNA}$ treatment enhanced the accumulation of polyfunctional tumor infiltrating CD8$^+$ T cells as indicated by comparing the number of IFN-γ TNF-α$^+$ double positive CD8$^+$ T cells.

SNA Structure Induces T Chap Exosomal Antigen Transfer for Bystander Priming.

Figure 8:
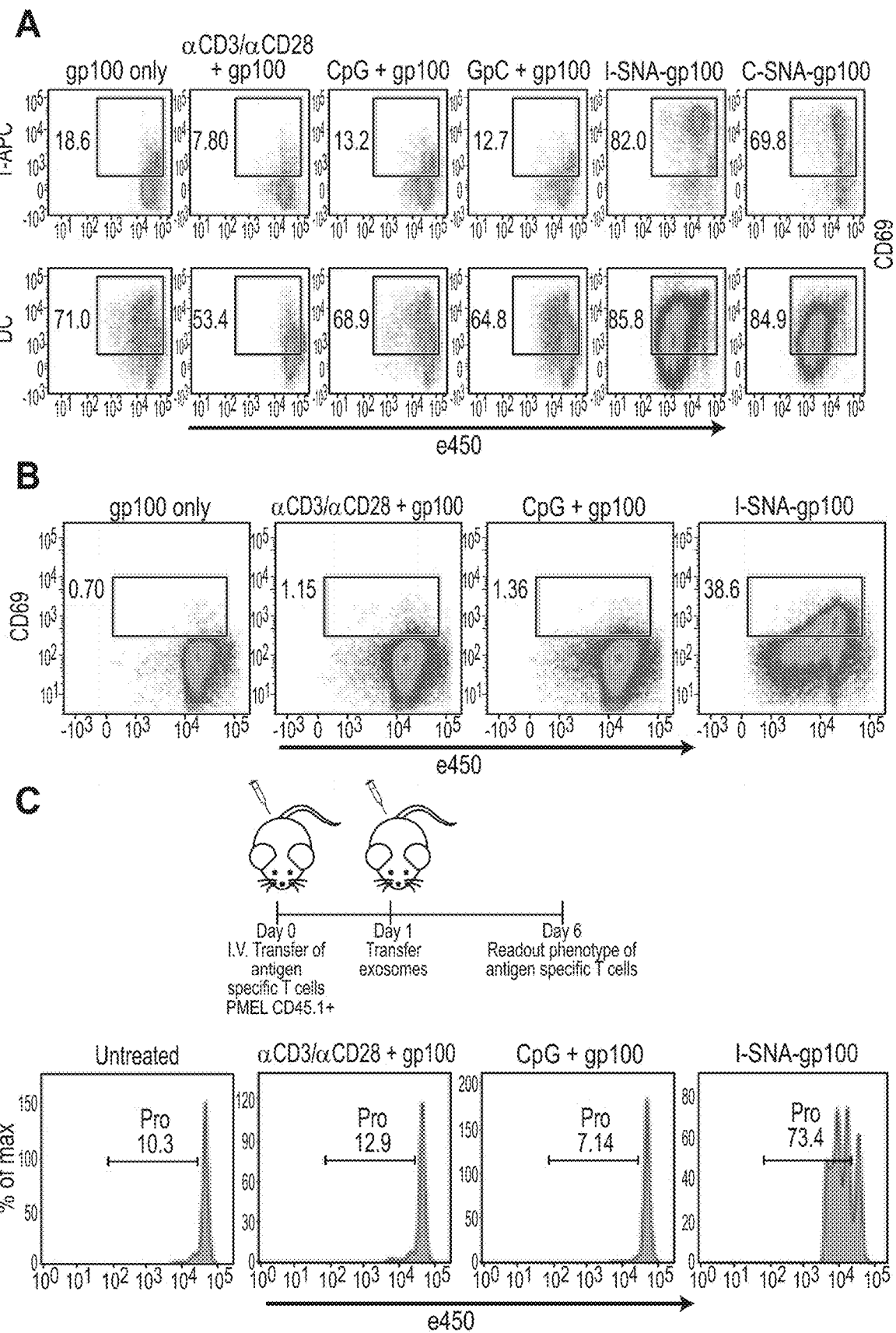
FIG. 8 shows that SNAs induce exosomal antigen transfer for bystander priming function. A) ISNA T chap exosomes transfer antigen to T cells and DCs in vitro. PMEL CD8$^+$ T cells were incubated with labeled conditions overnight. The next day they were washed and seeded in the top portion of a transwell system with 0.4 μm pores. The bottom wells contained naïve CD8⁺ PMEL T cells or naïve DCs. After 24 hours the cells from the bottom wells were isolated and used in priming assays with naïve e450 stained CD8+CD45.1⁺ PMEL T cells. T-APCs and DCs were plated at a 1:1 ratio with naïve responder cells. After four days, CD45.1⁺ cells were analyzed for activation markers using flow cytometry. B) ISNA T chap exosomes directly activate PMEL CD8⁺ T cells. Isolated T cells were incubated with the indicated conditions overnight. The next day they were washed and re-plated with exosome free medium. 10 μg of exosomes were then added directly to naïve e450 stained CD8⁺ for four days. Cells were then analyzed by flow cytometry. C) ISNA T chap exosomes induce T cell priming in vivo. On day 0 naïve e450 labeled CD8⁺ T cells were intravenously transferred into WT mice. On day 1, 30 μg of T cell derived exosomes were transferred intravenously. On day 6 Vβ13⁺ e450+CD8⁺ T cells were examined for proliferation by flow cytometry.

The goal of the experiments that led to the collection of data in FIG. 8 was to gain insight into the mechanism of T chap-induced priming. Whether T chaps were able to transfer antigen to dendritic cells through soluble factors was tested first. T chaps and two types of bystander recipient cells (T-cells and DCs) were separated using a transwell system where T chaps were placed in the top well and separated by a membrane with 0.4 µm pores. This experiment tested for the possibility that T cells are able to pass these soluble factors to other (naïve) T cells and endow them with the ability to become antigen presenting T cells (T-APC). After overnight transwell incubation the recipient cells, the recipient T-APC and DCs were able to prime CD45.1$^+$ PMEL T (FIG. 8A), showing that exosomal transfer of antigen to both T cells and DCs is one way in which T chaps induce priming.

Whether exosomes were able to directly induce T cells priming was tested next. CD8$^+$ PMEL T cells were activated and exosomes were collected after four days of culture. The exosomes were then directed plated with naïve e450 stained PMEL responder cells, and activation and proliferation were studied after four days. It was found that only exosomes derived from T chap$_{ISNA}$ induced CD69 expression and proliferation (FIG. 8B). Whether T chap derived exosomes are capable of initiating T cell priming in vivo was then tested. After transfer of naïve e450 labeled CD8$^+$ PMEL T cells, an equal amount of exosomes isolated from T chaps were also transferred i.v. After five days, only the exosomes from T chap$_{ISNA}$ induced proliferation of the naïve CD8$^+$ PMEL T cells in inguinal lymph nodes (FIG. 8C).

CONCLUSIONS

Currently, adoptive T cell therapy in clinical settings involves lengthy, expensive and potentially dangerous use of transfection reagents to modify T cells. The three dimensional structure of SNAs allows for rapid cellular entry through receptor mediated endocytosis, bypassing the need for transfection reagents [Cutler et. al., Journal of the American Chemical Society. 2012; 134(3):1376-91]. Recently, it was discovered that non-phagocytic T cells can rapidly and efficiently uptake spherical nucleic acids (SNAs) into the cytoplasm. The present disclosure used SNAs as a programming platform for the creation of cellular T cell chaperones, which possess unique anti-tumor capabilities. SNAs, as a cellular programming platform, have allowed for the successful creation of a multi-functional T cell chaperone that is capable of directly killing tumor cells, directly priming tumor antigen specific T cells, and transferring SNA materials (e.g., antigen and CpG oligonucleotide) to other immune cells via exosomes in vivo.

T chap$_{ISNA}$ showed superior performance in these activities over T chaps prepared from linear CpG/free peptide admix. In all side by side experiments, T chap$_{ISNA}$ dramatically outperformed their counter parts. In many cases, only T chap$_{ISNA}$ groups exhibited any phenotype, and were the only T chap to retain durable effector function in vitro and in vivo. These data indicated that SNAs are a formulation of immunestimulatory oligonucleotide and antigen that are particularly capable of inducing a long term and stable programming of T chaps, allowing them to resist the suppressive mechanisms in the tumor microenvironment which induces exhaustion and anergy. This is supported by the accumulation of poly-functional T cells in tumor tissue capable of producing IFN-γ and TNF-α in T chap$_{ISNA}$ tumor bearing animals. Additionally, T chap$_{ISNA}$ were capable of initiating an anti-tumor cascade through exosomal antigen sharing. This feature allowed for the dissemination of SNA material in tumor draining lymph nodes and in the tumor microenvironment. It is important that dendritic cells (DCs), professional antigen presenting cells, were able to act as recipient bystander cells and gain priming function. This served as a way to amplify T chap$_{ISNA}$ induced anti-tumor immunity. A final feature demonstrated here was the ability of T chap$_{ISNA}$ to act as T-APCs by priming naïve antigen specific T cells. Antigen presentation by T cells is poorly studied, but according to the data provided herein, may play a previously underappreciated role in expanding antigen specific T cells.

By using two different tumor models with different model antigens (B16/gp100 and LLC1OVA/OVA-I) it was demonstrated herein that the effect of T chap$_{ISNA}$ is not limited by a particular antigen. Due to the structure of SNAs, any antigen that is desired can be incorporated into the hollow core of SNAs for uptake by T cells and other immune cells. This means that this technology can be used against all forms of solid and liquid tumors. Furthermore, the effects disclosed herein were only tested using CpG oligonucleotides. As with antigen, SNAs can be customized to program cellular recipients by modification of hybridization style, length, and sequences. These include use of both DNA and RNA oligonucleotide sequences to target various toll-like receptors.

tor (TLR) agonist on the surface of the nanoparticle, and a tumor associated antigen, thereby producing an immune response to cancer in the individual.

3. The method of claim 1, wherein the nanoparticle is a liposome.

4. The method of claim 1, wherein the oligonucleotide comprises RNA or DNA.

5. The method of claim 1, wherein the oligonucleotide comprises a CpG nucleotide sequence.

6. The method of claim 1, wherein the nanoparticle has a diameter of 50 nanometers or less.

7. The method of claim 1, wherein the composition comprising about 10 to about 80 double stranded oligonucleotides.

8. The method of claim 1, wherein the tumor associated antigen is encapsulated in the nanoparticle, or wherein the tumor associated antigen is on the surface of the nanoparticle.

9. The method of claim 1, wherein the composition further comprises an additional oligonucleotide.

10. The method of claim 9, wherein the additional oligonucleotide comprises RNA or DNA.

11. The method of claim 10, wherein the additional oligonucleotide is capable of hybridizing to a polynucleotide encoding a gene and the additional oligonucleotide is complementary to all or a portion of the polynucleotide, wherein hybridizing between the polynucleotide and the oligonucleotide occurs over a length of the polynucleotide with a degree of complementarity sufficient to inhibit expression of the gene product.

12. The method of claim 11, wherein the RNA is an inhibitory RNA (RNAi).

What is claimed is:

1. A method of treating lung cancer or melanoma in an individual comprising administering to the individual a composition comprising a pharmaceutically acceptable carrier and a T cell having a spherical nucleic acid (SNA) contained therein, wherein the T cell is obtained from an individual and the SNA comprises a nanoparticle, an immunostimulatory oligonucleotide comprising a sequence that is a toll-like receptor (TLR) agonist on the surface of the nanoparticle, and a tumor associated antigen.

2. A method of producing an immune response to lung cancer or melanoma in an individual, comprising administering to the individual an effective amount of a composition comprising a pharmaceutically acceptable carrier and a T cell having a spherical nucleic acid (SNA) contained therein, wherein the T cell is obtained from an individual and the SNA comprises a nanoparticle, an immunostimulatory oligonucleotide comprising a sequence that is a toll-like recep- 13. The method of claim 12, wherein the RNAi is selected from the group consisting of a small inhibitory RNA (siRNA), a single-stranded RNA (ssRNA) that forms a triplex with double stranded DNA, and a ribozyme.

14. The method of claim 11, wherein the RNA is a microRNA.

15. The method of claim 11, wherein the DNA is an anti-sense DNA.

16. The method of claim 11, wherein expression of the gene product is inhibited in vivo, or wherein expression of the gene product is inhibited in vitro.

17. The method of claim 11, wherein the gene is programmed death 1 (PD-1) or programmed death-ligand 1 (PD-L1).

18. The method of claim 2, wherein the nanoparticle is a liposome.

19. The method of claim 2, wherein the oligonucleotide comprises RNA or DNA.

20. The method of claim 2, wherein the oligonucleotide comprises a CpG nucleotide sequence.

21. The method of claim 2, wherein the nanoparticle has a diameter of 50 nanometers or less.

22. The method of claim 2, wherein the composition comprising about 10 to about 80 double stranded oligonucleotides.

23. The method of claim 2, wherein the tumor associated antigen is encapsulated in the nanoparticle, or wherein the tumor associated antigen is on the surface of the nanoparticle.

24. The method of claim 2, wherein the composition further comprises an additional oligonucleotide.

25. The method of claim 24, wherein the additional oligonucleotide comprises RNA or DNA.

26. The method of claim 25, wherein the additional oligonucleotide is capable of hybridizing to a polynucleotide encoding a gene and the additional oligonucleotide is complementary to all or a portion of the polynucleotide, wherein hybridizing between the polynucleotide and the oligonucleotide occurs over a length of the polynucleotide with a degree of complementarity sufficient to inhibit expression of the gene product.

27. The method of claim 26, wherein the RNA is an inhibitory RNA (RNAi).

28. The method of claim 27, wherein the RNAi is selected from the group consisting of a small inhibitory RNA (siRNA), a single-stranded RNA (ssRNA) that forms a triplex with double stranded DNA, and a ribozyme.

29. The method of claim 26, wherein the RNA is a microRNA.

30. The method of claim 26, wherein the DNA is an anti-sense DNA.

31. The method of claim 26, wherein expression of the gene product is inhibited in vivo, or wherein expression of the gene product is inhibited in vitro.

32. The method of claim 26, wherein the gene is programmed death 1 (PD-1) or programmed death-ligand 1 (PD-L1).

* * * * *

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
ttgcagtcct tgcagtacct                                                           20